US012742182B2

(12) United States Patent
Akahata et al.

(10) Patent No.: US 12,742,182 B2
(45) **Date of Patent: *Sep. 22, 2026**

(54) CYTOKINE IMMUNOTHERAPY

(71) Applicant: VLP Therapeutics, Inc., Wilmington, DE (US)

(72) Inventors: Wataru Akahata, Kensington, MD (US); Jonathan F. Smith, Redwood City, CA (US)

(73) Assignee: VLP Therapeutics, Inc., Wilmington, DE (US)

(*) Notice: Subject to any disclaimer, the term of this patent is extended or adjusted under 35 U.S.C. 154(b) by 204 days.

This patent is subject to a terminal disclaimer.

(21) Appl. No.: 18/809,221

(22) Filed: Aug. 19, 2024

(65) Prior Publication Data

US 2024/0401081 A1 Dec. 5, 2024

Related U.S. Application Data

(63) Continuation of application No. 17/242,916, filed on Apr. 28, 2021, now Pat. No. 12,134,777.

(60) Provisional application No. 63/017,993, filed on Apr. 30, 2020.

(51) Int. Cl.

| | |
|---|---|
| ***C12N 15/86*** | (2006.01) |
| ***A61K 9/48*** | (2006.01) |
| ***A61K 9/51*** | (2006.01) |
| ***A61K 38/00*** | (2006.01) |
| ***A61P 35/00*** | (2006.01) |
| ***C07K 14/54*** | (2006.01) |

(52) U.S. Cl.

CPC ............ *C12N 15/86* (2013.01); *A61K 9/4825* (2013.01); *A61K 9/5123* (2013.01); *A61P 35/00* (2018.01); *C07K 14/5434* (2013.01); *A61K 38/00* (2013.01); *C12N 2770/36143* (2013.01)

(58) Field of Classification Search

CPC .......... C12N 15/86; C12N 2770/36143; A61K 9/4825; A61K 9/5123; A61K 38/00; C07K 14/5434

See application file for complete search history.

(56) References Cited

U.S. PATENT DOCUMENTS

| | | |
|---|---|---|
| 5,185,440 A | 2/1993 | Davis et al. |
| 5,439,809 A | 8/1995 | Haynes et al. |
| 5,505,947 A | 4/1996 | Johnston et al. |
| 5,580,773 A | 12/1996 | Kang et al. |

(Continued)

FOREIGN PATENT DOCUMENTS

| | | |
|---|---|---|
| AU | 2007317347 B2 | 5/2009 |
| CA | 3111440 A1 | 2/2020 |

(Continued)

OTHER PUBLICATIONS

Zika virus fact sheet, updated Sep. 6, 2016; URL:http://www.who.int/mediacentre/factsheets/zika/en/ ( 5 pages total).

(Continued)

*Primary Examiner* — Trevor Love
(74) *Attorney, Agent, or Firm* — Sughrue Mion, PLLC

(57) ABSTRACT

Provided herein is a novel immunologically-active alphavirus replicon vector which comprises a nucleic acid encoding alphavirus nonstructural proteins nsp1-4 and a cytokine protein(s)/polypeptide(s), which is useful for the treatment of a cancer and/or an inflammatory disease.

18 Claims, 7 Drawing Sheets

Specification includes a Sequence Listing.

(56) References Cited

U.S. PATENT DOCUMENTS 5,629,204 A 5/1997 Honjo et al.
5,639,650 A 6/1997 Johnston et al.
5,643,576 A 7/1997 Johnston et al.
5,698,520 A 12/1997 Honjo et al.
5,792,462 A 8/1998 Johnston et al.
5,811,407 A 9/1998 Johnston et al.
5,939,598 A 8/1999 Kucherlapati et al.
6,008,035 A 12/1999 Johnston et al.
6,156,558 A 12/2000 Johnston et al.
6,521,235 B2 2/2003 Johnston et al.
6,531,135 B1 3/2003 Johnston et al.
6,541,010 B1 4/2003 Johnston et al.
6,583,121 B1 6/2003 Johnston et al.
6,783,939 B2 8/2004 Olmsted
6,844,188 B1 1/2005 MacDonald et al.
6,982,087 B2 1/2006 Johnston et al.
7,045,335 B2 5/2006 Smith et al.
7,078,218 B2 7/2006 Smith et al.
7,101,550 B2 9/2006 Wood et al.
7,235,235 B2 6/2007 Johnston et al.
7,419,674 B2 9/2008 Chulay et al.
7,425,337 B2 9/2008 Smith et al.
7,442,381 B2 10/2008 Smith et al.
7,531,180 B2 5/2009 Polo et al.
7,572,453 B2 8/2009 Polo et al.
7,595,048 B2 9/2009 Honjo et al.
7,790,181 B2 9/2010 Platteborze et al.
8,158,418 B2 4/2012 Polo et al.
8,263,092 B1 9/2012 Smith et al.
8,460,913 B2 6/2013 Kamrud et al.
8,617,533 B2 12/2013 Smith et al.
8,680,258 B2 3/2014 Coffield et al.
8,709,441 B2 4/2014 Rayner et al.
9,079,943 B2 7/2015 Rayner et al.
9,187,729 B2 11/2015 Depaz et al.
9,249,191 B2 2/2016 Ueno et al.
9,255,126 B2 2/2016 Polo et al.
9,353,353 B2 5/2016 Nabel et al.
9,363,353 B1 6/2016 Chik
9,416,370 B2 8/2016 Smith et al.
9,441,247 B2 9/2016 Rayner et al.
9,487,563 B2 11/2016 Nabel et al.
9,512,190 B2 12/2016 Ueno et al.
9,597,414 B2 3/2017 Coffield, III et al.
9,637,532 B2 5/2017 Akahata et al.
9,969,986 B2 5/2018 Akahata et al.
10,098,943 B2 10/2018 Akahata et al.
10,111,943 B2 10/2018 Smith et al.
10,434,187 B2 10/2019 Coffield, III et al.
2003/0108521 A1 6/2003 Calatrava
2003/0232324 A1 12/2003 Polo et al.
2005/0214321 A1 9/2005 Rasochova et al.
2007/0122378 A1 5/2007 Freeman et al.
2008/0025067 A1 1/2008 Scheuerlein
2009/0079185 A1 3/2009 Carbines-Evans et al.
2009/0298955 A1 12/2009 Handa et al.
2009/0305950 A1 12/2009 Minato et al.
2009/0312190 A1 12/2009 Chinea Santiago et al.
2011/0027306 A1 2/2011 Rayner et al.
2011/0035004 A1 2/2011 Maxwell
2011/0081341 A1 4/2011 Honjo et al.
2011/0207223 A1 8/2011 Tang et al.
2011/0262389 A1 10/2011 Mosco
2011/0318373 A1 12/2011 Sasikumar et al.
2012/0003266 A1 1/2012 Nable et al.
2013/0122262 A1 5/2013 Nagakura et al.
2013/0251744 A1 9/2013 Ueno et al.
2014/0120125 A1 5/2014 Ella et al.
2014/0127247 A1 5/2014 Dubensky, Jr. et al.
2014/0170186 A1 6/2014 Nabel et al.
2014/0363458 A1 12/2014 Ueno et al.
2015/0017194 A1 1/2015 Akahata et al.
2016/0040134 A1 2/2016 Akahata et al.
2016/0074501 A1 3/2016 Akahata et al.
2016/0090403 A1 3/2016 Ueno et al.
2016/0200775 A1 7/2016 Akahata et al.
2016/0303221 A1 10/2016 Nabel et al.
2017/0035871 A1 2/2017 Ueno et al.
2017/0065703 A1 3/2017 Akahata et al.
2017/0233450 A1 8/2017 Akahata et al.
2017/0252425 A1 9/2017 Akahata et al.
2019/0185822 A1 6/2019 Akahata et al.
2020/0109178 A1 4/2020 Dehart et al.

FOREIGN PATENT DOCUMENTS

CN 102321639 A 1/2012
CN 106085974 A 11/2016
JP 4-506301 A 11/1992
JP 2007-512842 A 5/2007
JP 2007-537761 A 12/2007
JP 2008-543774 A 12/2008
WO 93/10152 A1 5/1993
WO 96/37616 A1 11/1996
WO 97/12048 A1 4/1997
WO 99/18226 A2 4/1999
WO 99/41383 A1 8/1999
WO 02/096939 A2 12/2002
WO 03/102166 A2 12/2003
WO 2004/043399 A2 5/2004
WO 2004/085660 A2 10/2004
WO 2006/040334 A1 4/2006
WO 2006/088229 A1 8/2006
WO 2007/003384 A1 1/2007
WO 2007/059715 A2 5/2007
WO 2007/100098 A1 9/2007
WO 2008/025067 A1 3/2008
WO 2009/079185 A2 6/2009
WO 2010/062396 A2 6/2010
WO 2011/035004 A1 3/2011
WO 2012/006180 A1 1/2012
WO 2012/023995 A1 2/2012
WO 2012/106356 A2 8/2012
WO 2012/123755 A1 9/2012
WO 2012/172574 A1 12/2012
WO 2013/009884 A1 1/2013
WO 2013/063248 A1 5/2013
WO 2013/122262 A1 8/2013
WO 2013/151764 A1 10/2013
WO 2014/170493 A2 10/2014
WO 2015/005500 A1 1/2015
WO 2015/139784 A1 9/2015
WO 2016/021209 A1 2/2016
WO 2016/048903 A1 3/2016
WO 2016/109792 A2 7/2016
WO 2016/199936 A1 12/2016
WO 2016/210127 A1 12/2016
WO 2017/009873 A1 1/2017
WO 2017/015463 A2 1/2017
WO 2018/068008 A1 4/2018
WO 2018/213731 A1 11/2018
WO 2019/124441 A1 6/2019

OTHER PUBLICATIONS

Zhang et al., "Vaccination with dengue virus-like particles induces humoral and cellular immune responses in mice", Virology Journal, 2011, 8:333, total 9 pages.

Yamaji et al. "Efficient production of Japanese encephalitis virus-like particles by recombinant lepidopteran insect cells" Appl. Microbiol Biotechnol, vol. 97, 2013 (pp. 1071-1079).

Adams et al., "The expression of hybrid HIV: Ty virus-like particles in yeast," Nature Sep. 3-9, 1987; 329(6134); pp. 68-70. (9 pages).

Advisory Action issued Sep. 9, 2020 in U.S. Appl. No. 16/225,181.

Akahata W., and G.J. Nabel, 2012, "A specific domain of the Chikungunya virus E2 protein regulates particle formation in human cells: implications for alphavirus vaccine design," J. Virol. 86(16): pp. 8879-8883.

Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pages total).

(56) References Cited

OTHER PUBLICATIONS

Allsopp CE et al., "Comparison of numerous delivery systems for the induction of cytotoxic T lymphocytes by immunization," Eur. J. Immunol., 1996, vol. 26, No. 8, pp. 1951-1959.
António Roldão et al., "Virus-like particles in vaccine development", Expert Rev. Vaccines, 2010, 9(10):, pp. 1149-1176.
Berthet et al. GenBank: AHF49783.1; 2015.
Birkett A et al. "A Modified Hepatitis B Virus Core Particle Containing Multiple Epitopes of the Plasmodium falciparum Circumsporozoite Protein Provides a Highly Immunogenic Malaria Vaccine in Preclinical Analyses in Rodent and Primate Hosts", Infection and Immunity, American Society for Microbiology, US, vol. 70, No. 12; Dec. 1, 2002, pp. 6860-6870.
Bonaldo et al., "Surface Expression of an Immunodominant Malaria Protein B Cell Epitope by Yellow Fever Virus", J. Mol. Biol., 315(4):873-885 (2002).
Bryce Chackerian et al., "Determinants of Autoantibody Induction by Conjugated Papillomavirus Virus-Like Particles", The Journal of Immunology, 2002, 169: pp. 6120-6126.
Calvo-Calle et al., "A Linear Peptide Containing Minimal T- and B-Cell Epitopes of Plasmodium falciparum Circumsporozoite Protein Elicits Protection against Transgenic Sporozoite Challenge", Infection and Immunity, Dec. 2006. vol. 74, No. 12. p. 6929-6939.
Carvalho et al., "Malaria Vaccine: Candidate Antigens, Mechanisms, Constraints and Prospects," Scand. J. Immunol., Blackwell Science Ltd. Jul. 1, 2002, vol. 56, pp. 327-343.
Charoensri et al. "An optimized expression vector for improving the yield of dengue virus-like particles from transfected insect cells" Journal of Virological Methods, vol. 205, 2014 (pp. 116-123).
Cox et al. "Predicting Zika virus structural biology: Challenges and opportunities for intervention" Antiviral Chemistry and Chemotherapy, vol. 24 (3-4), 2015 (pp. 118-126).
Crompton et al., "Advances and Challenges in malaria vaccine development," Science in medicine, The Journal of Clinical Investigation, Dec. 2010, vol. 120, No. 12, pp. 4168-4178.
De Wispelaere Melissanne, et al., "Mutagenesis of the DI/DIII Linker in Dengue Virus Envelope Protein Impairs Viral Particle Assembly", Journal of Virology, 2012, vol. 86, No. 13, pp. 7072-7083, ISSN: 0022-538X, Abstract, Fig.1, Fig.8-9, p. 7073.
Dobano C et al., Alphavirus replicon particles are highly immunogenic in the murine Malaria model by homologous or heterologous immunization, Open Vaccine Journal, vol. 1, 2008, pp. 27-37.
Elizabeth V.L. Grgacic et al., "Virus-like particles: Passport to immune recognition", Methods, 2006, 40: pp. 60-65.
Enfissi et al. GenBank: ALX35659.1, 2016.
F. Notka et al., "Accelerated clearance of SHIV in rhesus monkeys by virus-like particle vaccines is dependent on induction of neutralizing antibodies", Vaccine, 2000, vol. 18, No. 3-4, p. 291-301.
Federico M., "Virus-like particles show promise as candidates for new vaccine strategies," Future Virol. (2010) 5(4); pp. 371-374.
Final Office Action issued Apr. 29, 2020 in U.S. Appl. No. 16/225,181.
Final Office Action issued Mar. 22, 2021 in U.S. Appl. No. 16/225,181.
Garmashova et al., Analysis of Venezuelan Equine Encephalitis Virus Capsid Protein Function in the Inhibition of Cellular Transcription, Journal of Virology, Dec. 2007, pp. 13552-13565.
Gary T. Jennings et al., "Immunodrugs: Therapeutic VLP-Based Vaccines for Chronic Diseases", Annu. Rev. Pharmacol. Toxicol., 2009, 49: pp. 303-326.
GenBank "Zika virus strain MR 766, complete genome" AY632535.2, Nov. 23, 2010 (6 pages total) Retrieved on May 16, 2017 Retrieved from the Internet, URL: <https://www.ncbi.nlm.nih.gov/nuccore/AY632535>.
GenBank: AAB02517.1, "structural polyprotein precursor Venezuelan equine encephalitis virus", dated Nov. 17, 2004, retrieved from https://www.ncbi.nlm.nih.gov/protein/AAB02517.1.
GenBank: AAW78190.1. circumsporozoite protein, partial Plasmodium falciparum. Dec. 29, 2006. (2 pages).
GenBank: ADG95942.1, structural polyprotein Chikungunya virus http://www.ncbi.nlm.nih.gov/protein/296124572?report=genbank&log$=protalign&blast_rank=2&FiID=PBR7NTOU015. Dec. 28, 2010.
Ghasparian A et al., Engineered synthetic virus-like particles and their use in vaccine delivery, Chembiochem, 2011, vol. 12, No. 1, pp. 100-109.
Gilbert SC et al., A protein particle vaccine containing multiple Malaria epitopes, Nat. Biotechnol., 1997, vol. 15, No. 12, pp. 1280-1284. (7 pages).
Gregory J. Atkins et al., "Therapeutic and prophylactic applications of alphavirus vectors", Expert Reviews in Molecular Medicine, 2008, 10(e33): pp. 1-17.
Gregson et al., "Phase 1 Trial of an Alhydrogel Adjuvanted Hepatitis B Core Virus-Like Particle Containing Epitopes of Plasmodium falciparum Circumsporozoite Protein.", PLoS ONE. Feb. 2008 | vol. 3 | Issue 2| e1556.
Gunther Spohn et al., "A Virus-Like Particle-Based Vaccine Selectively Targeting Soluble TNF-a Protects from Arthritis without Inducing Reactivation of Latent Tuberculosis", The Journal of Immunology, 2007, 178: pp. 7450-7457.
Haddow A. D. et al., "Genetic Characterization of Zika Virus Strains: Geographic Expansion of the Asian Lineage" PLOS Neglected Tropical Disease, Feb. 2012, vol. 6, Issue 2, e1477 (7 pages total).
Heinz F et al., "Flaviviruses and flavivirus vaccines", Vaccine 30 (2012) 4301-4306.
Heinz Leibl et al., "Adjuvant/carrier activity of inactivated tick-borne encephalitis virus", Vaccine, 1998, 16(4): pp. 340-345.
Hevey et al., "Marburg Virus Vaccines Based upon Alphavirus Replicons Protect Guinea Pigs and Nonhuman Primates", Virology, 251: 28-37 (1998).
Hsieh Szu-Chia et al. "The length of and nonhydrophobic residues in the transmembrane domain of dengue virus envelope protein are critical for its retention and assembly in the endoplasmic reticulum" Journal of Virology, vol. 84 No. 9, Apr. 2010 (pp. 4782-4797).
Hsieh Szu-Chia, et al., "A strong endoplasmic reticulum retention signal in the stem-anchor region of envelope glycoprotein of dengue virus type 2 affects the production of virus-like particles", Virology, 2008, vol. 374, No. 2, pp. 338-350, ISSN: 0042-6822.
Huang Claire Y.H., et al., "The dengue virus type 2 envelope protein fusion peptide is essential for membrane fusion", Virology, 2010, vol. 396, No. 2, pp. 305-315, ISSN:0042-6822, Table, Fig.5, pp. 310-313.
International Search Report and Written Opinion issued Jul. 27, 2021 in International Application No. PCT/JP2021/017078.
International Search Report and Written Opinion, dated Mar. 26, 2019, issued by the International Searching Authority in PCT/JP2018/046794.
Ira Mellman et al., "Cancer immunotherapy comes of age," Nature, 2011, vol. 480 (pp. 480-489).
Jones RM et al., A plant-produced Pfs25 VLP Malaria Vaccine Candidate Induces Persistent Transmission Blocking Antibodies against Plasmodium falciparum in immunized mice, PLoS One, Nov. 18, 2013, vol. 8, No. 11, e79538, doi: 10.1371/journal.pone.0079538.
Jose et al. A Structural and functions perspective of alphavirus replication and assembly Future Microbiol, 2009, vol. 4, No. 7, pp. 837-856.
Kathy D. McCoy et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., 1999, 189(7): pp. 1157-1162.
Kevin C. Conlon et al., Cytokines in the Treatment of Cancer, Journal of Interferon & Cytokine Research, vol. 39, No. 1, 2019, pp. 6-21.
Khetarpal Niyati, et al., "Dengue-specific subviral nanoparticles: design, creation and characterization", Journal of Nanobiotechnology, 2013, vol. 11, No. 15, total 8 pages, ISSN: 1477-3155.
Kostyuchenko V et al., "Structure of the thermally stable Zika virus", Nature, May 19, 2016, vol. 533, pp. 425-428.
Kuo, S.-C., et al., 2012, Cell-based analysis of Chikungunya virus E1 protein in membrane fusion, J. Biomed. Sci. 19(44): pp. 1-12.

(56) References Cited

OTHER PUBLICATIONS

Larocca et al., "Vaccine Protection Against Zika Virus from Brazil", Nature, Aug. 25, 2016, 536(7617), 474-478, doi:10.1038/nature18952 (24 pages total).
Lechner F et al., Virus-like particles as a modular system for novel vaccines, Intervirology, 2002, vol. 45, No. 4-6, pp. 212-217.
Lin et al., "Analysis of Epitopes on Dengue Virus Envelope Protein Recognized by Monoclonal Antibodies and Polyclonal Human Sera by a High Throughput Assay", PLOS, Jan. 2012, 6(1):e1447, total 12 pages.
Liu et al., "Recombinant dengue virus-like particles from Pichia pastoris: efficient production and immunological properties," Vir. Genes, 2010: 40:53-59.
Malaria Vaccine Program, http://www.globalvaccines.org/content/malaria+vaccine+program/19614, 4 pages total (2012).
Manjila, et al., "Novel gene delivery systems", International Journal of Pharmaceutical Investigation, vol. 3, Issue 1, Jan. 2013 (7 pages).
Maria Lia Palomba et al., "CD8+ T-Cell-Dependent Immunity Following Xenogeneic DNA Immunization against CD20 in a Tumor Challenge Model of B-Cell Lymphoma", Clinical Cancer Research, 2005, 370(11): pp. 370-379.
Metz et al., PLoS ONE, 2011, vol. 6, Issue 10, pp. 1-10.
Milich D R et al. "Conversion of poorly immunogenic malaria repeat sequences into a highly immunogenic vaccine candidate", Vaccine, Elsevier Ltd, GB; vol. 20, No. 5-6; Dec. 12, 2001; pp. 771-788.
Non-Final Office Action issued Oct. 16, 2020 in U.S. Appl. No. 16/225,181.
Non-Final Office Action issued Oct. 2, 2019 in U.S. Appl. No. 16/225,181.
Oliveira GA et al., Safety and enhanced immunogenicity of a Hepatitis B core particle Plasmodium falciparum Malaria vaccine formulated in adjuvant montanide ISA 720 in a Phase I Trial, Infect. Immun., 2005, vol. 73, No. 6, pp. 3587-3597.
Oliveira-Ferreira et al., "Immunogenicity of Ty-VLP bearing a CD8(+) T cell epitope of the CS protein of P. yoelii: enhanced memory response by boosting with recombinant vaccinia virus.", Vaccine. Mar. 6, 2000; 18(17); 1863-1869.
Osada et al., Co-delivery of antigen and IL-12 by Venezuelan equine encephalitis virus replicon particles enhances antigen-specific immune responses and antitumor effects, Cancer Immunol Immunother, 2012 vol. 61, pp. 19411951.
Palucha et al., "Virus-Like Particles: Models for Assembly Studies and Foreign Epitope Carriers," Progress in Nucleic Acid Research and Molecular Biology, 2005, vol. 30, pp. 135-168.
Pan, W. Y. et al., Cancer Immunotherapy Using a Membrane-bound Interleukin-12 With B7-1 Transmembrane and Cytoplasmic Domains, Mol. Ther., 2012, vol. 20, No. 5, pp. 927-937.
Pfeiffer B et al., A virosome-mimotope approach to synthetic vaccine design and optimization: synthesis, conformation, and immune recognition of a potential Malaria-vaccine candidate, Angew. Chem. Int. Ed., 2003, vol. 42, No. 21, pp. 2368-2371. (5 pages).
Purdy D et al., "Secretion of noninfectious dengue virus-like particles and identification of amino acids in the stem region involved in intracellular retention of envelope protein" Virology, 2005, vol. 333, No. 2, pp. 239-250, ISSN: 0042-6822, Abstract, Fig. 1-4. Table 1, pp. 240, 247-248.
Pushko, et al., Replicon-Helper Systems from Attenuated Venezuelan Encephalitis Virus: Expression of Heterologous Genes in Vitro and Immunization against Heterologous Pathogens in Vivo, Virology 239, 1997 (pp. 389-401).
Richner et al. "Modified mRNA vaccines protect against Zika Virus infection" Cell, vol. 168., Mar. 9, 2017 , pp. 1114-1125, (23 pages total).
Rodion Gorchakov et al., "Comparative analysis of the alphavirus-based vectors expressing Rift Valley fever virus glycoproteins," Virology, vol. 366 (2007), pp. 212-225.
Rodrigues M et al., Influenza and Vaccinia viruses expressing Malaria CD8+T and B Cell epitopes. Comparison of their immunogenicity and capacity to induce protective immunity, J. Immunol., 1994, vol. 153, No. 10, pp. 4636-4648. (15 pages).
Rodriguez D et al., Vaccine Efficacy against malaria by the Combination of Porcine Parvovirus-Like Particles and Vaccinia Virus Vectors Expressing CS of Plasmodium, PLoS One, 2012.04.17, vol. 7, No. 4, e34445. (pp. 1-10).
Seligman S, "Constancy and diversity in the flavivirus fusion peptide", BioMed Central, Virology Journal 2008, Feb. 14, 2008, total 10 pages. URL: http://www.virologyj.com/content/5/1/27.
Shiratsuchi T. et al. "Replacing adenoviral vector HVR1 with a malaria B cell epitope improves immunogenicity and circumvents preexisting immunity to adenovirus in mice", Journal of Clinical Investigation; vol. 120, No. 10; Oct. 2010; pp. 3688-3701.
Sigrid Elshuber et al., "Cleavage of protein prM is necessary for infection of BHK-21 cells by tick-borne encephalitis virus," Journal of General Virology (2003) vol. 84, pp. 183-191.
Sigrid Elshuber et al., "Resuscitating Mutations in a Furin Cleavage-Deficient Mutant of the Flavivirus Tick-Borne Encephalitis Virus," Journal of Virology, vol. 79, No. 18, Sep. 2005, pp. 11813-11823.
Simona Ozden et al., "Inhibition of Chikungunya Virus Infection in Cultured Human Muscle Cells by Furin Inhibitors," Journal of Biological Chemistry, vol. 283, No. 32, Aug. 8, 2008 (10 pages total).
Siyang Sun et al: "Structural analyses at pseudo atomic resolution of Chikungunya virus and antibodies show mechanisms of neutralization", eLIFE, Apr. 2, 2013, vol. 2, pp. 1-27.
Taylor et al. "Production of immunogenic West Nile virus-like particles using a herpes simplex virus 1 recombinant vector" Virology, vol. 496, 2016 (pp. 186-193).
Taylor et al. Mutation of the N-Terminal Region of Chikungunya Virus Capsid Protein: Implications for Vaccine Design, Feb. 21, 2017, vol. 8(1), pp. e01970-16.
Tsai et al., "Complexity of Neutralizing Antibodies against Multiple Dengue Virus Serotypes after Heterotypic Immunization and Secondary Infection Revealed by In-Depth Analysis of Cross-Reactive Antibodies", Journal of Virology, Jul. 2015, vol. 89, No. 14, pp. 7348-7362.
U. Arora et al., "Virus-like particles displaying envelope domain III of dengue virus type 2 induce virus-specific antibody response in mice", Vaccine, Jan. 2013, vol. 31, No. 6, p. 873-878.
Urakami et al., "Development of a Novel Virus-Like Particle Vaccine Platform That Mimics the Immature Form of Alphavirus," Clinical and Vaccine Immunology, 24(7): e00090-17 (pp. 1-14).
Veltrop-Duits et al., "Human CD4+ T cells stimulated by conserved adenovirus 5 hexon peptides recognize cells infected with different species of human adenovirus", Eur. J. Immunol., 2006, vol. 36, pp. 2410-2423 (14 pages total).
Vitrop-Duits et al., Human CD4+T cells stimulated by conserved adenovirus 5 hexon peptides recognize cells infected with different species of human adenovirus, Eur. J. Immunol. 2006, vol. 36, pp. 2410-2423.
Vuola et al., "Differential Immunogenicity of Various Heterologous Prime-Boost Vaccine Regimens Using DNA and Viral Vectors in Healthy Volunteers", J. Immunol., 174(1):449-455 (2005).
Wataru Akahata et al., "A VLP vaccine for epidemic Chikungunya virus protects non-human primates against infection," Nat. Med., 2010, 16(3); 334-338. (pp. 1-12).
Wendy K. Roberts et al., "Vaccination with CD20 peptides induces a biologically active, specific immune response in mice", Blood, 2002, 99: pp. 3748-3755.
WHO Dengue vaccine research, "Immunization, Vaccines and Biologicals", http://www.who.int/immunization/research/development/dengue_vaccines/en/ (total 3 pages).
Y. Agata et al., "Expression of the PD-1 antigen on the surface of stimulated mouse T and B lymphocytes," International Immunology, 1996, vol. 8, No. 5, pp. 765-772.
Extended European Search Report issued Dec. 6, 2024 in Application No. 21797719.8.

Fig. 6a

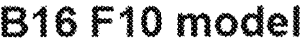
Fig. 8
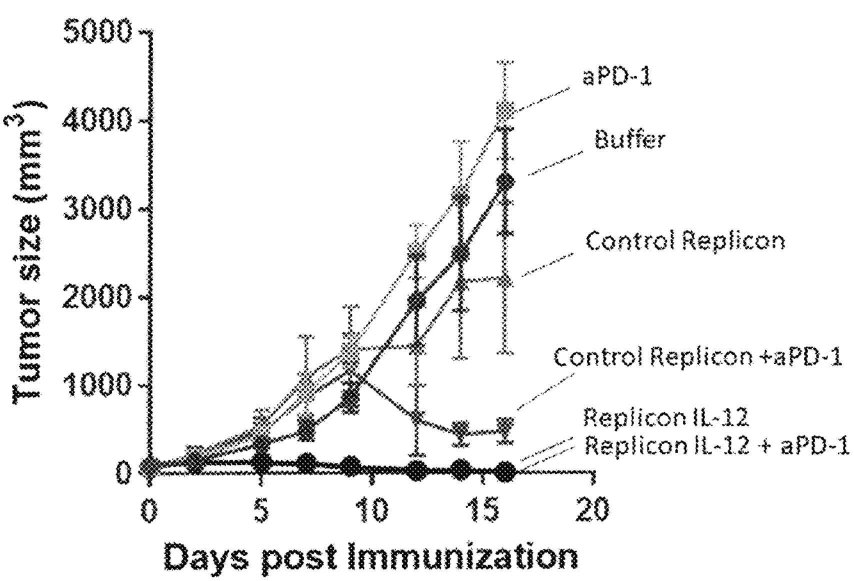
B16 F10 model
Tumor size (mm3)
5000
4000
3000
2000
1000
0
0
5
10
15
20
Days post Immunization
aPD-1
Buffer
Control Replicon
Control Replicon +aPD-1
Replicon IL-12
Replicon IL-12 + aPD-1

CYTOKINE IMMUNOTHERAPY

CROSS REFERENCE TO RELATED APPLICATIONS

This is a Rule 53(b) Continuation Application of U.S. application Ser. No. 17/242,916 filed Apr. 28, 2021, claiming priority based on U.S. Provisional Patent Application No. 63/017,993 filed Apr. 30, 2020, the contents of all of which are incorporated herein by reference in their entirety.

INCORPORATION BY REFERENCE OF SEQUENCE LISTING

The content of the electronically submitted sequence listing, file name: Q300835sequencelistingasfiled.xml; size 41,700 bytes; and date of creation: Aug. 18, 2024, filed herewith, is incorporated herein by reference in its entirety.

TECHNICAL FIELD

The present disclosure relates generally to the field of a cytokine immunotherapy against cancer and/or inflammatory disease, specifically to an alphavirus replicon vector comprising a cytokine which is useful for the treatment of a cancer and/or an inflammatory disease.

BACKGROUND ART

Cytokines are molecular messengers of the innate and adaptive immunity that enable cells of the immune system to communicate over short distances, and play critical roles in regulating all aspects of immune responses, including lymphoid development, homeostasis, differentiation, tolerance and memory. Considering the ability of the immune system to recognize and destroy cancer cells, there has been considerable interest over the past decades in harnessing cytokines for the treatment of cancer.

Preclinical experiments with interferon (IFNa), alpha granulocyte-macrophage colony stimulating factor (GM-CSF), interleukin (IL)-2, IL-12, IL-15, and IL-21 have shown efficacy in multiple murine cancer models.

IFNa was the first cytokine approved for the treatment of human cancer, hairy cell leukemia (HCL) in 1986, and after evaluating many treatment regimens, high-dose IL-2 (HDIL-2) was approved for the treatment of metastatic renal cell carcinoma (mRCC) in 1992, and metastatic melanoma (MM) in 1998. Since the initial approval, IFNa has added indications for follicular lymphoma, adjuvant melanoma, mRCC combined with bevacizumab, and AIDS-related Kaposi's sarcoma. Nevertheless, cytokines as monotherapy have not fulfilled the initial excitement they induced.

Strategies to address the issue of local versus systemic effects have included local or cavitary cytokine administration and transduction of stimulating or effector cells with genes encoding the cytokine through plasmid or viral delivery to augment the modest success with cytokine monotherapy. Other new approaches include structure-based cytokine engineering to generate "superkines" with increased binding affinity for select receptors to increase antitumor responses and proportionately decrease stimulation of Tregs. The development of chimeric antibody-cytokine fusion proteins and infusion of anticytokines in association with cytokines improve their tumor localization and pharmacokinetics compared to the native molecule. Additional clinical investigations combine cytokines with anticancer vaccines, checkpoint inhibitor (CPI) antibodies (anti-CTLA-4 or anti-PD-1/PD-L1), and the injection of cytokines with cancer-directed monoclonal antibodies to increase the antibody-dependent cellular cytotoxicity (ADCC) of these antibodies, thereby augmenting their antitumor efficacy (Non Patent literature 1: Kevin C. Conlon et. al, JOURNAL OF INTERFERON & CYTOKINE RESEARCH Volume 39, Number 1, 2019, the contents of the document is herein incorporated by reference).

IL-12 is a 70 kDa heterodimeric cytokine comprised of two disulfide-linked proteins, IL-12A p35 (35 kDa) and IL-12B p40 (40 kDa), naturally produced by dendritic cells, macrophages, neutrophils, and human B-lymphoblastoid cells (NC-37) and is essential for the initiation of effective immune response.

IL-12 has emerged as one of the most potent agents for anticancer immunotherapy. Local IL-12 expression consistently appears to be one of the most effective methods to overcome the immune suppression due to its central role in T- and NK-cell-mediated inflammatory responses. However, clinical application of IL-12-based therapies remains problematic due to the potential lethal toxicity associated with systemic administration.

Oncolytic viruses encoding IL-12 have demonstrated strong anti-tumor effects in preclinical models of cancers (Non-Patent Literature 2: Pan, W. Y. et al., Mol. Ther. 20 (5), 927-937 (2012), the contents of this document are herein incorporated by reference), however, systemic accumulation of IL-12 after delivery by oncolytic viruses remains potentially lethal to patients. Inefficient transduction of tumor cells with carrier vectors currently limits the overall anti-tumor effect of this approach.

More promising drug-inducible IL-12 systems are expected to manage the IL-12 levels over long periods with reducing level of toxicity for the clinical use.

CITATION LIST

Non Patent Literature 1

Kevin C. Conlon et. al, JOURNAL OF INTERFERON & CYTOKINE RESEARCH Volume 39, Number 1, 2019

Non Patent Literature 2

Pan, W. Y. et al., Mol. Ther. 20 (5), 927-937 (2012)

SUMMARY OF INVENTION

The present disclosure relates to an improved cytokine immunotherapy against cancer and/or inflammatory disease.

Specifically, the present disclosure relates to a novel immunologically-active alphavirus replicon vector comprising, a polynucleotide which encodes alphavirus non-structural proteins nsp1, nsp2, nsp3 and nsp4 and a polypeptide comprising a cytokine. The vector is useful for the treatment of cancer and/or inflammatory disease while minimizing toxicity.

In another aspect, the present disclosure provides a composition comprising the above discussed alphavirus replicon vector and a pharmaceutically acceptable carrier. The pharmaceutically acceptable carrier may be a delivery vehicle, wherein the vector is encapsulated in the delivery vehicle. In preferred embodiments, the delivery vehicle may an be alphavirus particle consisting of alphavirus structural proteins that may include capsid and/or envelope proteins. In another embodiment, the delivery vehicle may be lipid nanoparticles (LNP).

In another aspect, the present disclosure provides the above discussed alphavirus replicon vector or the composition for use in the treatment or immunization against cancer or inflammatory disease.

In another aspect, the present disclosure provides a use of the above discussed alphavirus replicon vector or the composition in the manufacture of a medicament for the treatment or immunization against cancer or inflammatory disease.

In another aspect, the present disclosure provides a method of treating and/or immunizing against cancer or inflammatory disease in a subject, which comprises administering an effective amount of the above discussed alphavirus replicon vector or composition to the subject in need thereof.

BRIEF DESCRIPTION OF DRAWINGS

FIG. 6*a* Effect of IL-12 alphavirus replicon constructed to express construct 6 on CT-26 tumor model mice.

FIG. 8 Effect of IL-12 alphavirus replicon constructed to express construct 1 on B16F10 tumor model mice.

DESCRIPTION OF EMBODIMENTS

Figure 1:
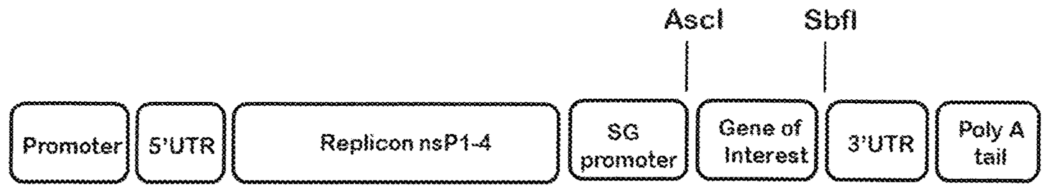
FIG. 1 A representative construct of an alphavirus replicon vector.

"Cytokine(s)" used herein is a polypeptide(s)/glycoprotein(s) derived from a natural lymphokine (cytokines made by lymphocytes), monokine (cytokines made by monocytes), chemokine (cytokines with chemotactic activities), an interleukin (cytokines made by one leukocyte and acting on other leukocytes), or modification thereof. The modified cytokine may be a fragment of the naturally occurring cytokine. In one embodiment, the modified cytokine has at least 70%, 75%, 80%, 85%, 90%, 95% or 98% amino acid sequence identity to a naturally occurring cytokine. In one embodiment, the modified cytokine is a mutant where at most 10% of the amino acids are deleted, substituted, and/or added based on a naturally occurring cytokine.

Examples of cytokines include, but are not limited to, interleukin (IL) including over 30 type such as IL-1α, IL-1β, IL-2, -3, -4, -5, -6, -7, -8, -9, -10, -11, -12, -13 to -37; interferon (IFN) such as IFN-α, IFN-5β and IFN-γ; tumor necrosis factor (TNF) such as TNF-α and TNF-β; transforming growth factor (TGF) such as TGF-α and TGF-β; colony stimulating factor (CSF) such as granulocyte-colony stimulating factor (G-CSF), granulocyte-macrophage-colony 10 stimulating factor (GM-CSF), macrophage-colony Stimulating factor (M-CSF), erythropoietin (EPO), stem cell factor (SCF) and monocyte chemotactic and activating factor (MCAF); growth factor (GF) such as epidermal growth factor (EGF), fibroblast growth factor (FGF), insulin like growth 15 factor (IGF), nerve growth factor (NGF), Brain-derived neurotrophic factor (BDNF), platelet derived growth factor (PDGF), vascular endothelial growth factor (VEGF), hepatocyte growth factor (HGF), keratinocyte growth factor (KGF), thrombopoietin (TPO), and bone morphogenic protein 20 (BMP); and other polypeptide factors including LIF, kit ligand (KL), MPO (Myeloperoxidase) and CRP (C-reactive protein); COX (Cyclooxygenase) such as COX-1, COX-2 and COX-3, NOS (Nitric oxide synthase) such as NOS-1, NOS-2 and NOS-3; and modified thereof.

Cytokines also includes chemokines which are cytokines that induce chemotaxis. There are two major classes of chemokines, CXC and CC. The CXC chemokines, such as neutrophil-activating protein-2 (NAP-2) and melanoma growth stimulatory activity 5 protein (MGSA) are chemotactic primarily for neutrophils and T lymphocytes, whereas the CC chemokines, such as RANTES, Macrophage inflammatory protein (MIP) including MIP-1α and MIP-1β, keratinocyte-derived chemokine (KC), the monocyte 10 chemotactic proteins (MCP-1, MCP-2, MCP-3, MCP-4, and MCP-5) and the eotaxins (−1 and −2) are chemotactic for, among other cell types, macrophages, T lymphocytes, eosinophils, neutrophils, dendritic cells, and basophils. There also exist the chemokines lymphotactin-1, lymphotactin-2 (both C15 chemokines), and fractalkine (a CX3C chemokine) that do not fall into either of the major chemokine subfamilies.

Preferable example of a cytokine is, but not limited to, IL-12.

In the alphavirus replicon vector of the present disclosure, the gene encoding a cytokine may be fused to a gene encoding a transmembrane domain. As used herein, "transmembrane domain (TM)" is a protein derived either from a natural or from a synthetic source. Where the source is natural, the domain in some aspects is derived from any membrane-bound or transmembrane protein. In one aspect, the membrane-bound or transmembrane protein is a protein heterologous to the cytokine. Examples of the membrane-bound or transmembrane proteins may include the alpha, beta or zeta chain of a T-cell receptor, CD28, CD3 epsilon, CD45, CD4, CD5, CD5, CD9, CD16, CD22, CD33, CD37, CD64, CD80, CD86, CD134, CD137, CD154; toll-like receptors (TLR) such as TLR1-TLR10 in human and TLR1-TLR9, TLR11-TLR13 in mouse; interleukin (IL) receptors such as IL-1-28 receptor, RANTES receptors (CCR1, CCR3, CCR5), MIP-1 receptor, PF4 receptor, M-CSF receptor and NAP-2 receptor belonging to GPCR chemokine receptor; hemagglutinin (HA).

Examples of transmembrane proteins may also include the followings:

5-Lipoxygenase-Activating Protein, ABC Transporters, ACBP, Amyloid beta (A4), Bcl-2 Inhibitors, BNIPs, CAAX protease, Cytochromes P450, E-NPPs, EPHA1, EPHA2, EPHA3, EPHA4, Fatty Acid Desaturases, Gamma secretase, Glucose transporter, Glycophorins, GPCR, HER2/ErbB2, HER3/ErbB3, HER4/ErbB4, HSD-11β, Hypoxia-induced Proteins, Immunoglobulins, Insulin receptor, Integrins, Ion channel, MAPEG, MFS, Mink Family, MPPs, Peptidase AD, Peptidase Family M48, Peptidase MA, Protein Jagged, Receptor-type Kinases, SNARE Complex, Sulfatases, TNF receptor, Transmembrane Proteins 14, Transporter, TROBP, VEGF receptors, Aldehyde Dehydrogenases, Ammonia and Urea transporters, FMN-linked Oxidoreductases, Leucine Rich Repeat (LRR)-Containing Transmembrane Proteins, Leukotriene C4 synthase, Lysosome-associated membrane glycoprotein, Major Intrinsic Protein (MIP)/FNT superfamily, Microsomal prostaglandin E synthase, N-(deoxy)ribosyltransferase-like Membrane Proteins, Neutral/alkaline Ceramidases, Oligosaccharyl Transferase, Pentameric Ligand-gated Ion Channels, Rhodopsin-like receptors and pumps, Single-helix ATPase Regulators, Squalene/phytoene Synthase, Stearoyl-CoA desaturase 1, Stannin (SNN) Membrane Proteins, T-cell Surface Glycoprotein CD3 Zeta Chain, Tetratricopeptide repeat (TPR) Alpha-Helical Repeat Proteins, Transmembrane Proteins with NAD(P)-binding Rossmann-fold Domains.

In addition, monotypic/peripheral proteins that attached to the lipid bilayer or other integral proteins and peptide may also be used as transmembrane proteins. Examples may include Alpha/Beta-Hydrolase, Annexins, Bet V1-Like Protein, C1 Domain-Containing Protein, C2 Domain-containing Protein, CoA-Dependent Acyltransferases, CRAL-TRIO Domain-Containing Protein, DNase I-like protein, Fibrinogen, FYVE/PHD Zinc Finger Protein, Galactose-Binding Domain-Like Protein, Glycolipid Transfer Protein, Immunoglobulin-Like Superfamily (E Set) Protein, Lipocalin, Lipoxygenase, PGBD superfamily, PH Domain-Like Protein, Phosphatidylinositol 3-/4-Kinase, PLC-like Phosphodiesterase, Phosphotyrosine Protein Phosphatases II, P-Loop Containing Nucleoside Triphosphate Hydrolase, Protein kinase superfamily, PX Domain-Containing Protein, Saposin, Synuclein and Transcriptional factor tubby.

The expression "transmembrane domain" used in the present disclosure includes at least transmembrane region(s) of the membrane-bound or transmembrane protein. In addition, the transmembrane domain may also include juxtamembrane domain (JMD) and/or cytoplasmic tail of the membrane-bound or transmembrane protein.

Alternatively the transmembrane domain in some embodiments is synthetic. In some aspects, the synthetic transmembrane domain comprises predominantly hydrophobic residues such as leucine and valine. There are also highly charged residues flanking the transmembrane domain (stop transport signals). There are also highly charged residues flanking the transmembrane domain (stop transport signals). In some aspects, a triplet of phenylalanine, tryptophan and valine will be found at each end of a synthetic transmembrane domain.

Preferable examples of transmembrane domain may be those derived from TLR4 (Toll-like receptor 4) and influenza virus hemagglutinin (HA). Specific examples may include a protein consisting of the flexible juxtamembrane region or flexible linker, the transmembrane domain and the cytoplasmic tail of Influenza virus hemagglutinin "HA (flexible-TM-Cyt)" and a protein consisting of TLR4 (Toll-like receptor 4).

By fusing the gene encoding a cytokine with gene encoding a transmembrane domain, especially with the influenza virus hemagglutinin transmembrane domain, the safety of the resulting alphavirus replicon vector will be improved while keeping the effect to induce immunological activities.

A cytokine polypeptide and a transmembrane domain may be directly or indirectly fused. In one embodiment, one or two linkers may intervene between them.

Also a cytokine polypeptide and a transmembrane domain can be truncated and replaced by short linkers. In some embodiments, a cytokine structural protein and a heterologous transmembrane domain include one or more peptide linkers.

An example of a short linker consists of from 2 to 25 amino acids (e.g. 2, 3, 4, 5 or 6 amino acids). Usually, it is from 2 to 15 amino acids in length, such as SG, GS, SGG, GGS SGSG and TRGGS. In certain circumstances, the linker can be only one, such as glycine (G), serine (S) and cysteine (C).

When a cytokine polypeptide is chemically conjugated to a heterologous transmembrane domain through a chemical cross-linker which is a chemical compound, the examples of the cross-linkers include, but are not limited to, SMPH, Sulfo-MBS, Sulfo-EMCS, Sulfo-GMBS, Sulfo-SIAB, Sulfo-SMPB, Sulfo-SMCC, SVSB and SIA.

IgG-derived substances can also be used as a linker. Examples of IgG-derived substances include IgG1 to IgG4 comprising (i) full (hinge-CH2CH3) (ii) half (hinge-CH3) and (iii) short (12aa hinge only). Preferable example is IgG4-CH3.

The construct may also comprise a signal sequence. As used herein, "signal sequence" (sometimes referred to as signal peptide, targeting signal, localization signal, localization sequence, transit peptide, leader sequence or leader peptide) is a polynucleotide or polypeptide, depending on the context. Signal sequence is from about 9 to 200 nucleotides or 3-70 amino acids in length that, optionally, is incorporated at the 5' or N-terminus of the coding region or the protein. Some signal sequences are cleaved from the protein, for example by a signal peptidase after the proteins are transported to the desired site.

The signal sequence may be of the target protein to be expressed by the alphavirus replicon.

As used herein "alphavirus" is meant to refer to RNA-containing viruses that belong to the Togaviridae family of viruses. Exemplary Togaviridae viruses include but are not limited to Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, Buggy Creek Virus and Ockelbo virus.

By "alphavirus structural protein" is meant a polypeptide or fragment thereof having at least about 80% amino acid sequence identity to a naturally occurring viral capsid or envelope protein. In one embodiment, the alphavirus structural protein has at least about 85%, 90%, 95% or greater amino acid sequence identity with Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, or Buggy Creek Virus. Wild type amino acid sequences of alphavirus structural proteins can be obtained from GenBank.

In specific embodiments, the alphavirus is a CHIKV, for example CHIKV strain 37997 or LR2006 OPY-1. In other embodiments, the alphavirus is a VEEV, for example VEEV strain TC-83.

By "alphavirus replicon" is meant an RNA molecule which can direct its own amplification in vivo in a target cell. The replicon encodes the polymerase(s) which catalyze RNA amplification (nsp1, nsp2, nsp3, nsp4) and contains cis RNA sequences required for replication which are recognized and utilized by the encoded polymerase(s). An alphavirus replicon typically contains the following ordered elements: 5' UTR, sequences which encode alphavirus nonstructural proteins (nsp1, nsp2, nsp3, nsp4), 3' UTR, and a poly A signal. An alphavirus replicon also contains one or more viral sub-genomic promoters directing the expression of the gene of interest. Those sequences may have one or more mutations taught in a prior art.

In this disclosure, “alphavirus replicon”, “alphavirus replicon vector” and “replicon” are used to refer the same substance.

An alphavirus replicon provided by the present disclosure may have the construct shown in FIG. 1.

By “alphavirus replicon particle” (ARP) is meant an alphavirus replicon packaged with alphavirus structural proteins. ARP does not contain polynucleotide encoding any of the alphavirus structural proteins.

In this disclosure, “comprises,” “comprising,” “containing” and “having” and the like can have the meaning ascribed to them in U.S. Patent law and can mean “includes”, “including,” and the like; “consisting essentially of or “consists essentially” likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By “fragment” is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide.

A fragment may contain 10, 20, 30, 40, 50, 60, 70, 80, 90, or 100, 200, 300, 400, 500, 600, 700, 800, 900, or 1000 nucleotides or amino acids.

By “reference” is meant a standard or control condition.

A “reference sequence” is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e<"3> and e<"100> indicating a closely related sequence.

By “effective amount” is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an “effective” amount.

A satisfactory effect may be obtained by systemic administration, e.g. intramuscular administration, intertumoral administration, subcutaneous administration or intravenous administration 1-8 times at the amount of $10^3$-$10^{10}$ Infectious Unit (IV) or 0.01-500 μg per time, preferably $10^5$-$10^{10}$ IU or 0.1-100 μg per time, for example $10^7$-$10^9$ IU or 1-50 μg per one time. The alphavirus replicon vector may preferably be formulated in a vaccine composition suitable for administration in a conventional manner.

By “subject” is meant a mammal, including, but not limited to, a human or non-human mammal, such as a bovine, equine, canine, ovine, or feline.

As used herein, the terms “treat,” treating,” “treatment,” and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms “prevent,” “preventing,” “prevention,” “prophylactic treatment” and the like refer to reducing the probability of developing a disorder or condition in a subject, who does not have, but is at risk of or susceptible to developing a disorder or condition.

Unless specifically stated or obvious from context, as used herein, the term “or” is understood to be inclusive.

Examples of cancer which may be treated include, but are not limited to, melanoma, renal cancer, prostate cancer, breast cancer, colon cancer and non-small cell lung cancer. Other examples of the cancer include, but are not limited to, include bone cancer, pancreatic cancer, skin cancer (e.g. melanoma), cancer of the head or neck, cutaneous or intraocular malignant melanoma, uterine cancer, ovarian cancer, rectal cancer, cancer of the anal region, stomach cancer, liver cancer, testicular cancer, carcinoma of the fallopian tubes, carcinoma of the endometrium, carcinoma of the cervix, carcinoma of the vagina, carcinoma of the vulva, Hodgkin’s Disease, non-Hodgkin’s lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis brain tumor, stem glioma, pituitary adenoma, Kaposi’s sarcoma, epidermoid cancer, squamous cell cancer, T-cell lymphoma, environmentally induced cancers including those induced by asbestos, and combinations thereof.

“Inflammatory disease” includes inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankylosing spondylitis, Reiter syndrome, reactive arthritis, psoriatic arthritis, juvenile idiopathic arthritis and enterophathis arthritis, enthesitis, hypersensitivity (including both airways hypersensitivity and dermal hypersensitivity) and allergies. Specific autoimmune diseases include autoimmune haematological disorders (including e.g. hemolytic anaemia, aplastic anaemia, pure red cell anaemia and idiopathic thrombocytopenia), systemic lupus erythematosus (SLE), lupus nephritis, inflammatory muscle diseases (dermatomyosytis), periodontitis, polychondritis, scleroderma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and irritable bowel syndrome), endocrine ophthalmopathy, Graves' disease, sarcoidosis, multiple sclerosis, systemic sclerosis, fibrotic diseases, primary biliary cirrhosis, juvenile diabetes (diabetes mellitus type I), uveitis, keratoconjunctivitis sicca and vernal keratoconjunctivitis, interstitial lung fibrosis, periprosthetic osteolysis, glomerulonephritis (with and without nephrotic syndrome, e.g. including idiopathic nephrotic syndrome or minimal change nephropathy), multiple myeloma other types of tumors, inflammatory disease of skin and cornea, myositis, loosening of bone implants, metabolic disorders, (such as obesity, atherosclerosis and other cardiovascular diseases including dilated cardiomyopathy, myocarditis, diabetes mellitus type II, and dyslipidemia), and autoimmune thyroid diseases (including Hashimoto thyroiditis), small and medium vessel primary vasculitis, large vessel vasculitides including giant cell arteritis, hidradenitis suppurativa, neuromyelitis optica, Sjögren's syndrome, Behcet's disease, atopic and contact dermatitis, bronchiolitis, inflammatory muscle diseases, autoimmune peripheral neurophaties, immunological renal, hepatic and thyroid diseases, inflammation and atherothrombosis, autoinflammatory fever syndromes, immunohematological disorders, and bullous diseases of the skin and mucous membranes. Anatomically, uveitis can be anterior, intermediate, posterior, or pan-uveitis. It can be chronic or acute. The etiology of uveitis can be autoimmune or non-infectious, infectious, associated with systemic disease, or a white-dot syndrome.

In any of the foregoing aspects, the method further comprises administering a second composition comprising a checkpoint inhibitor polypeptide or polynucleotide encoding the same, and an optional pharmaceutically acceptable carrier. In some aspects, the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab.

Unless specifically stated or obvious from context, as used herein, the terms "a", "an", and "the" are understood to be singular or plural.

The art will acknowledge that polynucleotide sequences described in the specification and claims will recite "T"s in a representative DNA sequence but where the sequence represents RNA, the "T"s would be substituted for "U"s.

Any compositions or methods provided herein can be combined with one or more of any of the other compositions and methods provided herein.

The term "vector" refers to the means by which a nucleic acid sequence can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Typically, the nucleic acid molecule to be expressed is "operably linked" to a promoter and/or enhancer, and is subject to transcription regulatory control by the promoter and/or enhancer.

In one embodiment, an RNA molecule such as an alphavirus replicon may be generated by conventional procedures known to the art from a template DNA sequence. In vitro transcription (IVT) methods permit template-directed synthesis of RNA molecules. IVT methods permit synthesis of large quantities of RNA transcript. Generally, IVT utilizes a DNA template comprising a promoter sequence upstream of a sequence of interest. The promoter sequence is most commonly of bacteriophage origin such as the T7, T3 or SP6 promoter sequence but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand. Kits for in vitro transcription such as T7 transcription kit (RiboMax™ Express Large Scale RNA production System, Promega (WI USA)).

The method of transfection and the choice of expression vehicle will depend on the host system selected. Transfection methods are described, e.g., in Ausubel et al. (supra); expression vehicles may be chosen from those provided, e.g., in Cloning Vectors: A Laboratory Manual (P. H. Pouwels et al., 1985, Supp. 1987) The references cited in this paragraph are herein incorporated by reference.

A variety of expression systems exist for the production of the constructs of the invention. Expression vectors useful for producing the constructs include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as alphavirus (e.g. Chikungunya Virus (CHIKV) and Venezuelan Equine Encephalitis Virus (VEEV)), baculoviruses, papova viruses, such as SV40, vaccinia viruses, adenoviruses, fowl pox viruses, pseudorabies viruses and retroviruses, and vectors derived from combinations thereof.

Constructs and/or alphavirus replicon vectors used herein comprise alphavirus polynucleotides that encode structural proteins, including envelope proteins or capsid protein as described herein. Also, constructs and/or vectors used herein comprise alphavirus polynucleotides that encode nonstructural proteins nsp1, nsp2, nsp3 and nsp4 and a gene of interest. Specific example of the construct or vector is that shown in FIG. 1.

The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBacl pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, can express viral proteins, including those described herein, into eukaryotic cells and/or prokaryotic cells. Thus, in one embodiment, the present disclosure provides for host cells which comprise a vector (or vectors) that contain nucleic acids which encode alphavirus structural proteins, including capsid, E3, E2, 6K, and E1 or portions thereof, and a vector that comprises nucleic acids which encode alphavirus nsp1, nsp2, nsp3 and nsp4, and at least one of gene of interest encoding a cytokine under conditions which allow the formation of alphavirus replicon particles. The term "alphavirus replicon particles" refers to particles consisting of alphavirus structural proteins in which the alphavirus replicon vector comprising polynucleotide encoding alphavirus nonstructural proteins nsp1, nsp2, nsp3 and nsp4 and a polypeptide comprising a cytokine is incorporated.

In one embodiment, said vector is a recombinant baculovirus.

In another embodiment, said recombinant baculovirus is transfected into an insect cell. In a preferred embodiment, said cell is an insect cell. In another embodiment, said insect cell is a Sf9 cell.

One particular bacterial expression system for polypeptide production is the *E. coli* pET expression system (Novagen, Inc., Madison, Wis). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved by using host strains that express T7 RNA polymerase in response to IPTG induction. Once produced, a recombinant polypeptide is then isolated according to standard methods known in the art, for example, those described herein.

Depending on the vectors and host cells selected, the constructs are produced by growing host cells transfected by the vectors under conditions whereby the recombinant proteins are expressed and the alphavirus replicon is generated, and constructs containing alphavirus replicon being packaged with the particle of alphavirus structural proteins are formed. In one embodiment, the invention comprises a method of producing a construct, that involves co-transfecting a vector comprising a polynucleotide encoding alphavirus non-structural protein nsp1, nsp2, nsp3 and nsp4, and at least one gene of interest encoding the polipeptide comprising a cytokine, at least one vector each encoding at least one alphavirus structural protein into suitable host cells and expressing said alphavirus structural protein under conditions that allow construct formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells that produce alphavirus replicon particles of the disclosure include, but are not limited to, batch, batch-fed, continuous and perfusion cell culture techniques. In one embodiment, cells co-transfected with a vector encoding an alphavirus replicon and a vector comprising a polypeptide encoding capsid, and a vector comprising a polynucleotide encoding envelope proteins, such as those derived from a CHIKV or VEEV are grown in a bioreactor or fermentation chamber where cells propagate and express protein (e.g., recombinant proteins) for purification and isolation. Typically, cell culture is performed under sterile, controlled temperature and atmospheric conditions. A bioreactor is a chamber used to culture cells in which environmental conditions such as temperature, atmosphere, agitation and/or pH can be monitored. In one embodiment, the bioreactor is a stainless steel chamber. In another embodiment, said bioreactor is a pre-sterilized plastic bag (e.g., Cellbag®, Wave Biotech, Bridgewater, N.J., the contents of the cited document is herein incorporated by reference). In other embodiment, said pre-sterilized plastic bags are about 50 L to 1000 L bags.

As used herein, the term "pharmaceutically acceptable carrier" means one or more compatible solid or liquid fillers, diluents or encapsulating substances which are suitable for administration to a human or other vertebrate animal, including any and all aqueous solvents (e.g., water, alcoholic/aqueous solutions, saline solutions, parenteral vehicles, such as sodium chloride, and Ringer's dextrose), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters. Encapsulating substances refers to a delivery vehicle where the polynucleotide or vector is packaged, such as a replicon particle (e.g. the alphavirus replicon particle described in US patent publication No. 2019-0185822, the contents of this document is herein incorporated by reference) and a lipid delivery system (e.g. liposome).

In some embodiments, the compositions or formulations of the present disclosure comprise a lipid delivery system, e.g., a liposome, lioplexes, a lipid nanoparticle, or any combination thereof. The alphavirus replicon vector described herein can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that may primarily be composed of a lipid bilayer and may be used as a delivery vehicle for the administration of pharmaceutical formulations. Liposomes can be of different sizes. A multilamellar vesicle (MLV) may be hundreds of nanometers in diameter, and may contain a series of concentric bilayers separated by narrow aqueous compartments. A small unicellular vesicle (SUV) may be smaller than 50 nm in diameter, and a large unilamellar vesicle (LUV) may be between 50 and 500 nm in diameter. Liposome design may include, but is not limited to, opsonins or ligands to improve the attachment of liposomes to unhealthy tissue or to activate events such as, but not limited to, endocytosis. Liposomes may contain a low or a high pH value in order to improve the delivery of the pharmaceutical formulations.

The formation of liposomes may depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

In some embodiments, the alphavirus replicon vector described herein may be encapsulated by the liposome and/or it may be contained in an aqueous core that may then be encapsulated by the liposome.

In some embodiments, the alphavirus replicon vector described herein can be formulated in a cationic oil-in-water emulsion where the emulsion particle comprises an oil core and a cationic lipid that can interact with the polynucleotide anchoring the molecule to the emulsion particle. In some embodiments, the vector described herein can be formulated in a water-in-oil emulsion comprising a continuous hydrophobic phase in which the hydrophilic phase is dispersed.

In some embodiments, the alphavirus replicon vector described herein can be formulated in a lipid-polycation complex. As a non-limiting example, the polycation can include a cationic peptide or a polypeptide such as, but not limited to, polylysine, polyornithine and/or polyarginine and the cationic peptides.

In some embodiments, the alphavirus replicon vector described herein can be formulated in a lipid nanoparticle (LNP).

Lipid nanoparticle formulations typically comprise one or more lipids. In some embodiments, the lipid is a cationic or an ionizable lipid. In some embodiments, lipid nanoparticle formulations further comprise other components, including a phospholipid, a structural lipid, a quaternary amine compound, and a molecule capable of reducing particle aggregation, for example a PEG or PEG-modified lipid. In some embodiments, the amount of the cationic and ionizable lipids in the lipid composition ranges from about 0.01 mol % to about 99 mol %.

LNPs contain a pH-sensitive ionizable cationic lipid that attract anionic nucleic acids to form the core of self-assembling nanoparticle to ensure high encapsulation. At physiological pH, LNPs are neutral, eliminating a mechanism of toxicity seen with permanently cationic molecules. These same pH-sensitive lipids are responsible for responding to the acidic environment of the endosome and triggering the disruption of the endosome and release of the nucleic acid into the cell.

This replicon based technology is a unique platform technology for the vaccination as a RNA can self-amplify to produce the vaccine antigen and deliver into the cellular organ. Moreover, this replicon based vaccine technology overcomes the challenges commonly associated with DNA based vaccines, such as risk of genome integration or the high doses and devices needed for administration, e.g. electroporation, and expects the higher immunogenicity with minimum dose based on the self-replication system over the mRNA technology.

According to the present disclosure, a novel immunologically-active alphavirus replicon vector which comprises a nucleic acid encoding a cytokine protein(s)/polypeptide(s), which is useful for the treatment of a cancer and/or an inflammatory disease while minimizing toxicity.

The invention will be described in detail with reference to the following examples, which, however, are not intended to limit the scope of the present application.

Example 1

Each gene encoding shown below constructs 1-6 was synthesized by Integrated DNA Technologies, Inc. (https://www.idtdna.com/pages).

Construct 1

Gene encoding Mouse IL-12 sequence described below.

[Chem. 1]

| ssmIL-12B | mIL12-B (p40 w/o SS) | linker | mIL12A (p35 w/o SS) |
|---|---|---|---|

(SEQ ID NO: 1)

```
MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNEKNKTFLKCEAPNYSGRFTCSWLVQRNMDL

KENIKSSSSPPDSRAVTCGMASLSAEKVTLDQRDYEKYSVSCQEDVTCPT
```

-continued

AEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED

LKMYQTEFQAINAALQNHNHQQIILDKGMLVAIDELMQSLNHNGETLRQK

PPVGEADPYRVKMKLCILLHAFSTRVVTINRVMGYLSSA

The linker is underlined.

Mouse IL-12B (p40)

(SEQ ID NO: 2)

MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNFKNKTFLKCEAPNYSGRFTCSWLVQRNMDL

KFNIKSSSSPPDSRAVTCGMASLSAEKVTLDQRDYEKYSVSCQEDVTCPT

AEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRS

Mouse IL-12A (35p) without Signal Sequence (SEQ ID NO: 3)

RVIPVSGPARCLSQSRNLLKTTDDMVKTAREKLKHYSCTAEDIDHEDITR

DQTSTLKTCLPLELHKNESCLATRETSSTTRGSCLPPQKTSLMMTLCLGS

IYEDLKMYQTEFQAINAALQNHNHQQIILDKGMLVAIDELMQSLNHNGET

LRQKPPVGEADPYRVKMKLCILLHAFSTRVVTINRVMGYLSSA

Linker (SEQ ID NO: 4)

VPGVGVPGVG

In the following constructs 2-6, "Mouse IL-12 (p40-p35)" corresponds to Construct 1.

Construct 2

Gene encoding Mouse IL-12 (p40-p35) fused to human IgG4CH3 and HA (flexible domain-Transmembrane (TM)-Cytoplasmic Tail (Cyt)) with linkers.

[Chem. 2]

Mouse IL-12 (p40-p35) | GS | Human IgG4CH3 | GS | HA (flex-TM-Cyt)

(SEQ ID NO: 5)

MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNEKNKTELKCEAPNYSGRETCSWLVQRNMDL

-continued

KENIKSSSSPPDSRAVTCGMASLSAEKVTLDQRDYEKYSVSCQEDVTCPT

AEETLPIELALEARQQNKYENYSTSFFIRDIIKPDPPKNLQMKPLKNSQV

EVSWEYPDSWSTPHSYFSLKFFVRIQRKKEKMKETEEGCNQKGAELVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED

LKMYQTEFQAINAALQNHNHQQIILDKGMLVAIDELMQSLNHNGETLRQK

PPVGEADPYRVKMKLCILLHAFSTRVVTINRVMGYLSSAGSGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGKGS

GVKLESMGIYQILAIYSTVASSLVLLVSLGAISFWMCSNGSLQCRICI

The underlined "GS" are linkers.

human IgG4 CH3:

(SEQ ID NO: 6)

GQPREPQVYTLPPSQEEMTKNQVSLTCLVKGFYPSDIAVEWESNGQPENN

YKTTPPVLDSDGSFELYSRLTVDKERWQEGNVESCSVMHEALHNHYTQKS

LSLSLGK

GS: linker (GGATCC)

HA (flexible-TM-Cyt):

(SEQ ID NO: 7)

GVKLESMGIYQILAIYSTVASSLVLLVSLGAISFWMCSNGSLQCRICI

Construct 3

Gene encoding Mouse IL-12 (p40-p35) fused to HA (flexible-TM-Cyt) with a linker

[Chem. 3]

Mouse IL-12 (p40-p35) | GS | HA (flex-TM-Cyt)

(SEQ ID NO: 8)

MACPQKLTISWFAIVLLVSPLMAMWELEKDVYVVEVDWTPDAPGETVNLT

CDTPEEDDITWTSDQRHGVIGSGKILTITVKEFLDAGQYTCHKGGETLSH

SHLLLHKKENGIWSTEILKNEKNKTFLKCEAPNYSGRFTCSWLVQRNMDL

KENIKSSSSPPDSRAVTCGMASLSAEKVTLDQRDYEKYSVSCQEDVTCPT

AEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED

LKMYQTEFQAINAALQNHNHQQIILDKGMLVAIDELMQSLNHNGETLRQK

-continued

```
PPVGEADPYRVKMKLCILLHAFSTRVVTINRVMGYLSSAGSGVKLESMGI

YQILAIYSTVASSLVLLVSLGAISFWMCSNGSLQCRICI
```

The underlined “GS” is a linker.

Construct 4

Gene encoding mouse IL-12 (p40-p35) fused to human IgG4CH3 and human TLR4 (TM-Toll/interleukin-1 receptor domain (TIR)) with linkers

[Chem. 4]

| Mouse IL-12 (p40-p35) | GS | Human IgG4CH3 | GS | human TLR4(TM-TIR) |
|---|---|---|---|---|

```
                                             (SEQ ID NO: 9)
MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNEKNKTFLKCEAPNYSGRETCSWLVQRNMDL

KENIKSSSSPPDSRAVTCGMASLSAEKVILDQRDYEKYSVSCQEDVTCPT

AEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED

LKMYQTEFQAINAALQNHNHQQIILDKGMLVAIDELMQSLNHNGETLRQK

PPVGEADPYRVKMKLCILLHAFSTRVVTINRVMGYLSSAGSGQPREPQVY

TLPPSQEEMTKNQVSLTCLVKGFYPSDIAVEWESNGQPENNYKTIPPVLD

SDGSFELYSRLTVDKSRWQEGNVESCSVMHEALHNHYTQKSLSLSLGKGS

KTIIGVSVLSVLVVSVVAVLVYKEYFHLMLLAGCIKYGRGENIYDAFVIY

SSQDEDWVRNELVKNLEEGVPPFQLCLHYRDFIPGVAIAANIIHEGFHKS

RKVIVVVSQHFIQSRWCIFEYEIAQTWQFLSSRAGIIFIVLQKVEKTLLR

QQVELYRLLSRNTYLEWEDSVLGRHIFWRRLRKALLDGKSWNPEGTVGTG

CNWQEATSI
```

The underlined “GS” are linkers.

```
human TLR4(TM-TIR):
                                            (SEQ ID NO: 10)
KTIIGVSVLSVLVVSVVAVLVYKFYFHLMLLAGCIK YGRGENIYDAFV

IYSSQDEDWVRNELVKNLEEGVPPFQLCLHYRDFIPGVAIAANIIHEGE

HKSRKVIVVVSQHFIQSRWCIFEYEIAQTWQFLSSRAGIIFIVLQKVEK

ILLRQQVELYRLLSRNTYLEWEDSVLGRHIFWRRLRKALLDGKSWNPEG

TVGTGCNWQEATSI
```

Construct 5

Gene encoding mouse IL-12 (p40-p35) fused to human TLR4 (TM-TIR) with linker

[Chem. 5]

| Mouse IL-12 (p40-p35) | GS | human TLR4(TM-TIR) |
|---|---|---|

```
                                            (SEQ ID NO: 11)
MACPQKLTISWFAIVLLVSPLMAMWELEKDVYVVEVDWTPDAPGETVNL

TCDTPEEDDITWTSDQRHGVIGSGKTLTITVKEFLDAGQYTCHKGGETL

SHSHLLLHKKENGIWSTEILKNEKNKTFLKCEAPNYSGRETCSWLVQRN

MDLKENIKSSSSPPDSRAVTCGMASLSAEKVTLDQRDYEKYSVSCQEDV

TCPTAEETLPIELALEARQQNKYENYSTSFFIRDIIKPDPPKNLQMKPL

KNSQVEVSWEYPDSWSTPHSYFSLKFFVRIQRKKEKMKETEEGCNQKGA

FLVEKTSTEVQCKGGNVCVQAQDRYYNSSCSKWACVPCRVRSVPGVGVP

GVGRVIPVSGPARCLSQSRNLLKTTDDMVKTAREKLKHYSCTAEDIDHE

DITRDQTSTLKTCLPLELHKNESCLATRETSSTTRGSCLPPQKTSLMMT

LCLGSIYEDLKMYQTEFQAINAALQNHNHQQIILDKGMLVAIDELMQSL

NHNGETLRQKPPVGEADPYRVKMKLCILLHAFSTRVVTINRVMGYLSSA

GSKTIIGVSVLSVLVVSVVAVLVYKFYFHLMLLAGCIKYGRGENIYDAF

VIYSSQDEDWVRNELVKNLEEGVPPFQLCLHYRDFIPGVAIAANIIHEG

FHKSRKVIVVVSQHFIQSRWCIFEYEIAQTWQFLSSRAGIIFIVLQKVE

KTLLRQQVELYRLLSRNTYLEWEDSVLGRHIFWRRLRKALLDGKSWNPE

GTVGTGCNWQEATSI
```

The underlined “GS” is a linker.

Construct 6

Gene encoding Mouse IL-12 (p40-p35) fused to Mouse IgG4CH3 and HA (flexible domain-Transmembrane (TM)-Cytoplasmic Tail (Cyt)) with linkers.

[Chem. 6]

| Mouse IL-12 (p40-p35) | GS | Mouse IgG4CH3 | GS | HA (flex-TM-Cyt) |
|---|---|---|---|---|

```
                                            (SEQ ID NO: 12)
MACPQKLTISWFAIVLLVSPLMAMWELEKDVYVVEVDWTPDAPGETVNL

TCDTPEEDDITWTSDQRHGVIGSGKTLTITVKEFLDAGQYTCHKGGETL

SHSHLLLHKKENGIWSTEILKNFKNKTFLKCEAPNYSGRFTCSWLVQRN

MDLKFNIKSSSSPPDSRAVTCGMASLSAEKVTLDQRDYEKYSVSCQEDV

TCPTAEETLPIELALEARQQNKYENYSTSFFIRDIIKPDPPKNLQMKPL

KNSQVEVSWEYPDSWSTPHSYFSLKFFVRIQRKKEKMKETEEGCNQKGA

FLVEKTSTEVQCKGGNVCVQAQDRYYNSSCSKWACVPCRVRSVPGVGVP
```

-continued

```
GVGRVIPVSGPARCLSQSRNLLKTTDDMVKTAREKLKHYSCTAEDIDHE
DITRDQTSTLKTCLPLELHKNESCLATRETSSTTRGSCLPPQKTSLMMT
LCLGSIYEDLKMYQTEFQAINAALQNHNHQQIILDKGMLVAIDELMQSL
NHNGETLRQKPPVGEADPYRVKMKLCILLHAFSTRVVTINRVMGYLSSA
GSGRPKAPQVYTIPPPKEQMAKDKVSLTCMITNFFPEDITVEWQWNGQP
AENYKNTQPIMDTDGSYFVYSKLNVQKSNWEAGNTFTCSVLHEGLHNHH
TEKSLSHSPGKGSGVKLESMGIYQILAIYSTVASSLVLLVSLGAISFWM
CSNGSLQCRICI
```

The underlined "GS" are linkers.

Mouse IgG4CH3

(SEQ ID NO: 13)

```
GRPKAPQVYTIPPPKEQMAKDKVSLTCMITNFFPEDITVEWQWNGQPAE
NYKNTQPIMDTDGSYFVYSKLNVQKSNWEAGNTFTCSVLHEGLHNHHTE
KSLSHSPG
```

HA (flexible-TM-Cyt) and IgG4 are also disclosed as follows.

HA (flexible-TM-Cyt)

https://www.ncbi.nlm.nih.gov/protein/P03452

UniProtKB/Swiss-Prot: P03452.2

Human IgG4 https://www.uniprot.org/uniprot/P01861

UniProtKB: P01861

Example 2

Each gene encoding Construct 7 and 8 was prepared.

Construct 7

Human IL-12 sequence described below.

[Chem. 7]

| SS hIL-12B | hIL-12B(p40 w/o SS) | Linker | hIL-12A(p35 w/o SS) |
|---|---|---|---|

(SEQ ID NO: 14)

```
MCHQQLVISWFSLVFLASPLVAIWELKKDVYVVELDWYPDAPGEMVVLT
CDTPEEDGITWTLDQSSEVLGSGKTLTIQVKEFGDAGQYTCHKGGEVLS
HSLLLLHKKEDGIWSTDILKDQKEPKNKTFLRCEAKNYSGRFTCWWLTT
ISTDLTFSVKSSRGSSDPQGVTCGAATLSAERVRGDNKEYEYSVECQED
SACPAAEESLPIEVMVDAVHKLKYENYTSSFFIRDIIKPDPPKNLQLKP
LKNSRQVEVSWEYPDTWSTPHSYFSLTFCVQVQGKSKREKKDRVETDKT
SATVICRKNASISVRAQDRYYSSSWSEWASVPCSVPGVGVPGVGRNLPV
ATPDPGMFPCLHHSQNLLRAVSNMLQKARQTLEFYPCTSEEIDHEDITK
DKTSTVEACLPLELTKNESCLNSRETSFITNGSCLASRKTSFMMALCLS
SIYEDLKMYQVEFKTMNAKLLMDPKRQIFLDQNMLAVIDELMQALNFNS
ETVPQKSSLEEPDFYKTKIKLCILLHAFRIRAVTIDRVMSYLNAS
```

The first underline represents the signal sequence (SS) of human IL-12B (p40) and the second underline represents a linker.

Human IL-12B (p40)

(SEQ ID NO: 15)

```
MCHQQLVISWFSLVFLASPLVAIWELKKDVYVVELDWYPDAPGEMVVLT
CDTPEEDGITWTLDQSSEVLGSGKTLTIQVKEFGDAGQYTCHKGGEVLS
HSLLLLHKKEDGIWSTDILKDQKEPKNKTFLRCEAKNYSGRFTCWWLTT
ISTDLTFSVKSSRGSSDPQGVTCGAATLSAERVRGDNKEYEYSVECQED
SACPAAEESLPIEVMVDAVHKLKYENYTSSFFIRDIIKPDPPKNLQLKP
LKNSRQVEVSWEYPDTWSTPHSYFSLTFCVQVQGKSKREKKDRVFTDKT
SATVICRKNASISVRAQDRYYSSSWSEWASVPCS
```

The underlined is the signal sequence (SS) of human IL-12B (p40).

Linker (underline)

(SEQ ID NO: 4)

```
VPGVGVPGVG
```

Human IL-12A (p35) w/o Signal Sequence (The signal sequence "MCPARSLLLVATLVLLDHLSLA (SEQ ID NO: 16)" is deleted)

(SEQ ID NO: 17)

```
RNLPVATPDPGMFPCLHHSQNLLRAVSNMLQKARQTLEFYPCTSEEIDH
EDITKDKTSTVEACLPLELTKNESCLNSRETSFITNGSCLASRKTSFMM
ALCLSSIYEDLKMYQVEFKTMNAKLLMDPKRQIFLDQNMLAVIDELMQA
LNFNSETVPQKSSLEEPDFYKTKIKLCILLHAFRIRAVTIDRVMSYLNA
S
```

Construct 8

Gene encoding human IL-12 (p40-p35) fused to human IgG4CH3 and HA (flexible domain-Transmembrane (TM)-Cytoplasmic Tail (Cyt)) with linkers.

[Chem. 8]

| Human IL-12 (p40-p35) | GS | Human IgG4CH3 | GS | HA (flex-TM-Cyt) |
|---|---|---|---|---|

In the above structure, "Human IL-12 (p40-p35)" corresponds to Construct 7.

(SEQ ID NO: 18)

```
MCHQQLVISWFSLVFLASPLVAIWELKKDVYVVELDWYPDAPGEMVVLT
CDTPEEDGITWTLDQSSEVLGSGKTLTIQVKEFGDAGQYTCHKGGEVLS
HSLLLLHKKEDGIWSTDILKDQKEPKNKTFLRCEAKNYSGRFTCWWLTT
```

-continued

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVETDKT

SATVICRKNASISVRAQDRYYSSSWSEWASVPCSVPGVGVPGVGRNLPV

ATPDPGMFPCLHHSQNLLRAVSNMLQKARQTLEFYPCTSEEIDHEDITK

DKTSTVEACLPLELTKNESCLNSRETSFITNGSCLASRKTSFMMALCLS

SIYEDLKMYQVEFKTMNAKLLMDPKRQIFLDQNMLAVIDELMQALNFNS

ETVPQKSSLEEPDFYKTKIKLCILLHAFRIRAVTIDRVMSYLNASGSGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGKGSGVKLESMGIYQILAIYSTVASSLVLLVSLGAISFWMCSNG

SLQCRICI

The underlined “GS” are linkers.

Human IL-12B (p40)
UniProt: P29460
https://www.uniprot.org/uniprot/P29460
Human IL-12A (p35)
Uniprot: P29459
https://www.uniprot.org/uniprot/P29459

Example 3

Preparation of Vector

Schematic construct of the alphavirus replicon is shown in FIG. 1.

Figure 2:
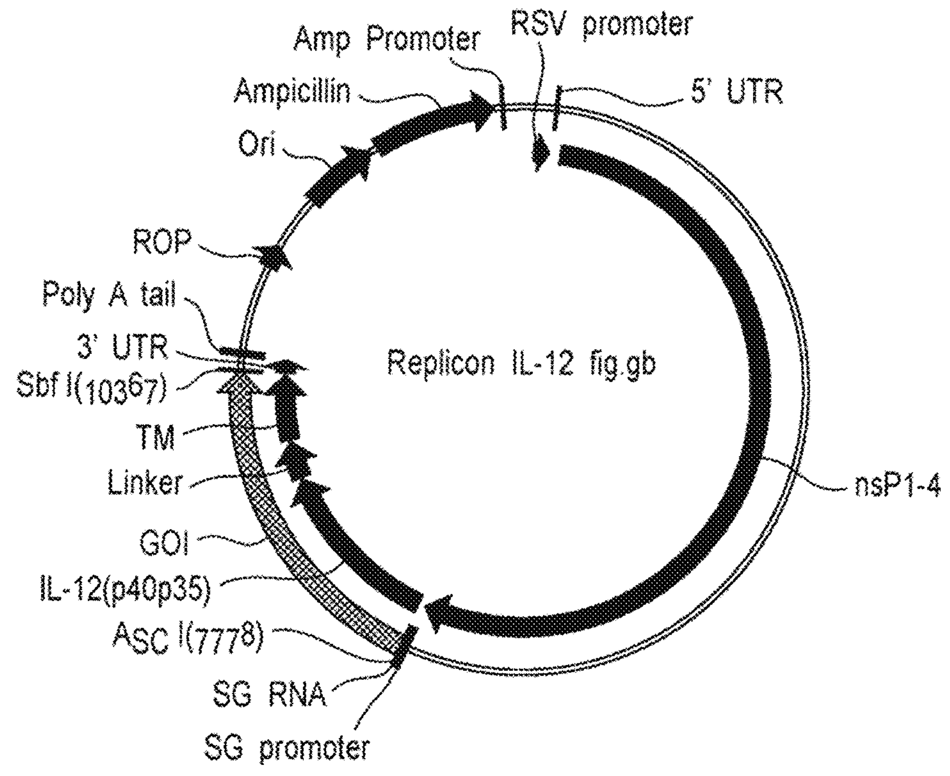
FIG. 2 Full length VEEV TC-83 vector of the construct including a polynucleotide encoding the construct comprising IL-12-Linker-TM produced in Example 3.

Each of constructs 1-6 prepared in Example 1 and constructs 7 and 8 prepared in Example 2 was used as gene of interest. Nucleotides encoding the construct was cloned into the VEEV replicon vector under the control of SG promoter. The VEEV replicon plasmid encoding each fragment was created by inserting AscI and SbfI restriction sites to obtain the full-length VEEV TC-83 replicon construct. See FIG. 2 for the construct with TM and FIG. 3 for the construct without TM.

Nucleotide sequences of SG promoter, 5'UTR, 3'UTR and Poly A tail are as follows. RNA sequences were obtained by using those DNA sequences as template.

SG promoter:

(SEQ ID NO: 19)

cctgaatggactacgacatagtctagtccgccaag

5 'UTR:

(SEQ ID NO: 20)

ataggcggcgcatgagagaagcccagaccaattacctacccaaa

3' UTR:

(SEQ ID NO: 21)

gcgatcgcatacagcagcaattggcaagctgcttacatagaactcgcggcgattggcat gccgccttaaaatttttattttatttttcttttcttttccgaatcggattttgtttttta atatttc Poly A tail:

(SEQ ID NO: 22)

aaaaaaaaaaaaaaaaaaaaaaaaaaaaaaaaaaaaaaaaaaaaaaaaaaaaaaa

VEEV TC-83 Replicon nsP1-4 amino acid sequence is as follows.

(SEQ ID NO: 23)

MEKVHVDIEEDSPFLRALQRSFPQFEVEAKQVTDNDHANARAFSHLASK

LIETEVDPSDTILDIGSAPARRMYSKHKYHCICPMRCAEDPDRLYKYAT

KLKKNCKEITDKELDKKMKELAAVMSDPDLETETMCLHDDESCRYEGQV

AVYQDVYAVDGPTSLYHQANKGVRVAYWIGFDTTPFMFKNLAGAYPSYS

TNWADETVLTARNIGLCSSDVMERSRRGMSILRKKYLKPSNNVLFSVGS

TIYHEKRDLLRSWHLPSVFHLRGKQNYTCRCETIVSCDGYVVKRIAISP

GLYGKPSGYAATMHREGFLCCKVTDTLNGERVSFPVCTYVPATLCDQMT

GILATDVSADDAQKLLVGLNQRIVVNGRTQRNTNTMKNYLLPVVAQAFA

RWAKEYKEDQEDERPLGLRDRQLVMGCCWAFRRHKITSIYKRPDTQTII

KVNSDFHSFVLPRIGSNTLEIGLRTRIRKMLEEHKEPSPLITAEDIQEA

KCAADEAKEVREAEELRAALPPLAADFEEPTLEADVDLMLQEAGAGSVE

TPRGLIKVTSYAGEDKIGSYAVLSPQAVLKSEKLSCIHPLAEQVIVITH

SGRKGRYAVEPYHGKVVVPEGHAIPVQDFQALSESATIVYNEREFVNRY

LHHIATHGGALNTDEEYYKTVKPSEHDGEYLYDIDRKQCVKKELVTGLG

LTGELVDPPFHEFAYESLRTRPAAPYQVPTIGVYGVPGSGKSGIIKSAV

TKKDLVVSAKKENCAEIIRDVKKMKGLDVNARTVDSVLLNGCKHPVETL

YIDEAFACHAGTLRALIAIIRPKKAVLCGDPKQCGFFNMMCLKVHFNHE

ICTQVFHKSISRRCTKSVTSVVSTLFYDKRMRTTNPKETKIVIDTTGST

KPKQDDLILTCFRGWVKQLQIDYKGNEIMTAASQGLTRKGVYAVRYKV

NENPLYAPTSEHVNVLLTRTEDRIVWKTLAGDPWIKILTAKYPGNFTAT

IEEWQAEHDAIMRHILERPDPTDVFQNKANVCWAKALVPVLKTAGIDMT

TEQWNTVDYFETDKAHSAEIVLNQLCVRETGLDLDSGLFSAPTVPLSIR

NNHWDNSPSPNMYGLNKEVVRQLSRRYPQLPRAVATGRVYDMNTGTLRN

YDPRINLVPVNRRLPHALVLHHNEHPQSDFSSFVSKLKGRTVLVVGEKL

SVPGKKVDWLSDQPEATFRARLDLGIPGDVPKYDIVFINVRTPYKYHHY

-continued

QQCEDHAIKLSMLTKKACLHLNPGGTCVSIGYGYADRASESIIGAIARQ

FKFSRVCKPKSSHEETEVLFVFIGYDRKARTHNPYKLSSTLTNIYTGSR

LHEAGCAPSYHVVRGDIATATEGVIINAANSKGQPGGGVCGALYKKFPE

SFDLQPIEVGKARLVKGAAKHIIHAVGPNFNKVSEVEGDKQLAEAYESI

AKIVNDNNYKSVAIPLLSTGIFSGNKDRLTQSLNHLLTALDTTDADVAI

YCRDKKWEMTLKEAVARREAVEEICISDDSSVTEPDAELVRVHPKSSLA

GRKGYSTSDGKTFSYLEGTKFHQAAKDIAEINAMWPVATEANEQVCMYI

LGESMSSIRSKCPVEESEASTPPSTLPCLCIHAMTPERVQRLKASRPEQ

ITVCSSFPLPKYRITGVQKIQCSQPILFSPKVPAYIHPRKYLVETPPVE

ETPESPAENQSTEGTPEQPALVNVDATRTRMPEPIIIEEEEEDSISLLS

DGPTHQVLQVEADIHGSPSVSSSSWSIPHASDFDVDSLSILDTLDGASV

TSGAVSAETNSYFARSMEFRARPVPAPRTVFRNPPHPAPRTRTPPLAHS

RASSRTSLVSTPPGVNRVITREELEALTPSRAPSRSASRTSLVSNPPGV

NRVITREEFEAFVAQQQXRFDAGAYIFSSDTGQGHLQQKSVRQTVLSEV

VLERTELEISYAPRLDQEKEELLRKKLQLNPTPANRSRYQSRRVENMKA

ITARRILQGLGHYLKAEGKVECYRTLHPVPLYSSSVNRAFSSPKVAVEA

CNAMLKENFPTVASYCIIPEYDAYLDMVDGASCCLDTASFCPAKLRSFP

KKHSYLEPTIRSAVPSAIQNTLQNVLAAATKRNCNVTQMRELPVLDSAA

FNVECFKKYACNNEYWETFKENPIRLTEENVVNYITKLKGPKAAALFAK

THNLNMLQDIPMDRFVMDLKRDVKVTPGTKHTEERPKVQVIQAADPLAT

ADLCGIHRELVRRLNAVLLPNIHTLFDMSAEDFDAIIAEHFQPGDCVLE

TDIASFDKSEDDAMALTALMILEDLGVDAELLTLIEAAFGEISSIHLPT

KTKFKFGAMMKSGMFLTLFVNTVINIVIASRVLRERLTGSPCAAFIGDD

NIVKGVKSDKLMADRCATWLNMEVKIIDAVVGEKAPYFCGGFILCDSVT

GTACRVADPLKRLFKLGKPLAVDDEHDDDRRRALHEESTRWNRVGILPE

LCKAVESRYETVGTSIIVMAMTTLASSVKSFSYLRGAPITLYG

Amino acid sequence corresponding to nsp3 is underlined.

In this example, amino acid sequence of nsp3 which is corresponding from 1330-1886 in SEQ ID NO: 23 was replaced with the sequence shown below. The underlined sequence was different from SEQ ID NO: 23.

(SEQ ID NO: 24)

APSYHVVRGDIATATEGVIINAANSKGQPGGGVCGALYKKFPESFDLQP

IEVGKARLVKGAAKHIIHAVGPNFNKVSEVEGDKQLAEAYESIAKIVND

NNYKSVAIPLLSTGIFSGNKDRLTQSLNHLLTALDTTDADVAIYCRDKK

WEMTLKEAVARREAVEEICISDDSSVTEPDAELVRVHPKSSLAGRKGYS

-continued

TSDGKTFSYLEGTKFHQAAKDIAEINAMWPVATEANEQVCMYILGKSMS

SIRSKCPVEESEASTPPSTLPCLCIHAMTPERVQRLKASRPEQITVCSS

FPLPKYRITGVQKIQCSQPILFSPKVPAYIHPRKYLVETPPVDETPEPS

AENQSTEGTPEQPPLITEDETRTRTPEPIIIEEEEEDSISLLSDGPTHQ

VLQVEADIHGPPSVSSSSWSIPHASDFDVDSLSILDTLEGASVTSGATS

AETNSYFAKSMEFLARPVPAPRTVFRNPPHPAPRTRTPSLAPSRACSRT

SLVSTPPGVNRVITREELEALTPSRTPSRSVSRTSLVSNPPGVNRVITR

EEFEAFVAQQQXRFDAGA

Example 4

Preparation of Alphavirus Replicon Particles (ARP)

10 μg of the full-length replicon plasmid for each of constructs 1-8 prepared in Example 3, 1 μg of VEEV Env expression plasmid and 1 μg of VEEV Capsid NLS mutant (or 1 μg VEEV Capsid expression plasmid) were transfected into HEK293T cells. The supernatant was harvested 48-96 hours after transfection. The replicon particles were purified by using an ion exchange column. The HEK293T or Vero cells was infected with the purified particles to determine the infectious titer. The purified replicon particles were used for the treatment of therapy.

Example 5

Effects of the Alphavirus Replicon Constructed to Express Construct 1

Figure 3:
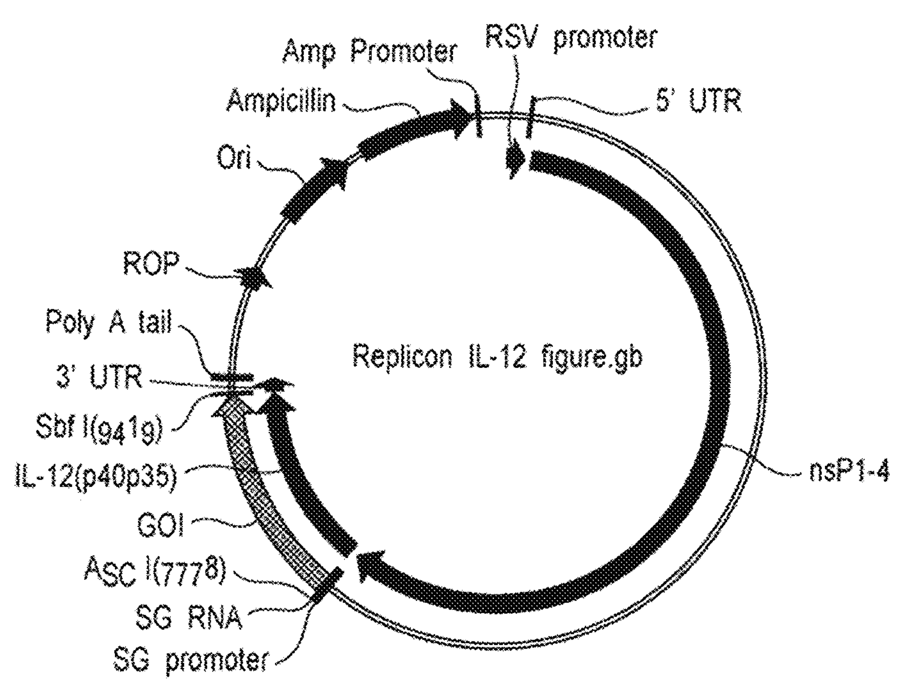
FIG. 3 Full length VEEV TC-83 vector of the construct including a polynucleotide encoding the construct comprising IL-12 produced in Example 3.

IL-12 alphavirus replicon particles prepared in Example 4 constructed to express construct 1 were evaluated. Mouse MC-38 subcutaneous syngeneic model was employed for the evaluation. MC-38 is a cell line derived from C57BL6 murine colon adenocarcinoma cells. C57BL/6 female mice (48 mice) were injected with $10^6$ cells, subcutaneously, into the rear flank. All mice were randomized into 6 groups (n=8 per group) when the average tumor volume reached 75-125 $mm^3$. Dosing was initiated within 24 hours of randomization (Day 0). Animals were dosed according to Table 1 below. The replicon Groups 3 and 4 assessed a control vector, constructed to express GFP as the gene of interest, and Groups 5 and 6 were constructed to express mouse IL-12 (Construct 1). The mice were injected with $1\times10^9$ infectious unit dose (IU) of the indicated replicon intratumorally (i.t.) at one day intervals (total of 8 times) or with 10 mg/kg of anti-mouse PD-1 monoclonal antibody (clone RMP1-14, aPD-1 mAb) given by intraperitoneal injection (IP) biweekly for a total of 6 times. Animals were monitored, and tumors measured twice weekly for the duration of the study. The results are shown in FIG. 3. FIG. 3 shows mean and errors (s.e.m.) of tumor size in each group.

TABLE 1

| Group | Treatment | N | Dose Route | Dosing Frequency & Duration | Dose Level (mg/kg) | Dose Volume (mL/kg) |
|---|---|---|---|---|---|---|
| 1 | Vehicle (TNE buffer) | 8 | i.t. | 0, 2, 4, 6, 8, 10, 12, 14 | NA | 50 ul for each dose (Fixed volume) |
| 2 | aPD-1 mAb | 8 | IP | BIWX3 weeks (Total 6 dose) | 10 | 5 |
| 3 | Control ARP (GFP) | 8 | i.t. | 0, 2, 4, 6, 8, 10, 12, 14 | $10^9$ IU/dose | 50 ul for each dose (Fixed volume) |
| 4 | Control ARP (GFP) | 8 | i.t. | 0, 2, 4, 6, 8, 10, 12, 14 | $10^9$ IU/dose | 50 ul for each dose (Fixed volume) |
| | aPD-1 mAb | 8 | IP | BIWX3 weeks (Total 6 dose) | 10 | 5 |
| 5 | ARP mIL-12 | 8 | i.t. | 0, 2, 4, 6, 8, 10, 12, 14 | $10^9$ IU/dose | 50 ul for each dose (Fixed volume) |
| 6 | ARP mIL-12 | 8 | i.t. | 0, 2, 4, 6, 8, 10, 12, 14 | $10^9$ IU/dose | 50 ul for each dose (Fixed volume) |
| | aPD-1 mAb | 8 | IP | BIWX3 weeks (Total 6 dose) | 10 | 5 |

Figure 4:
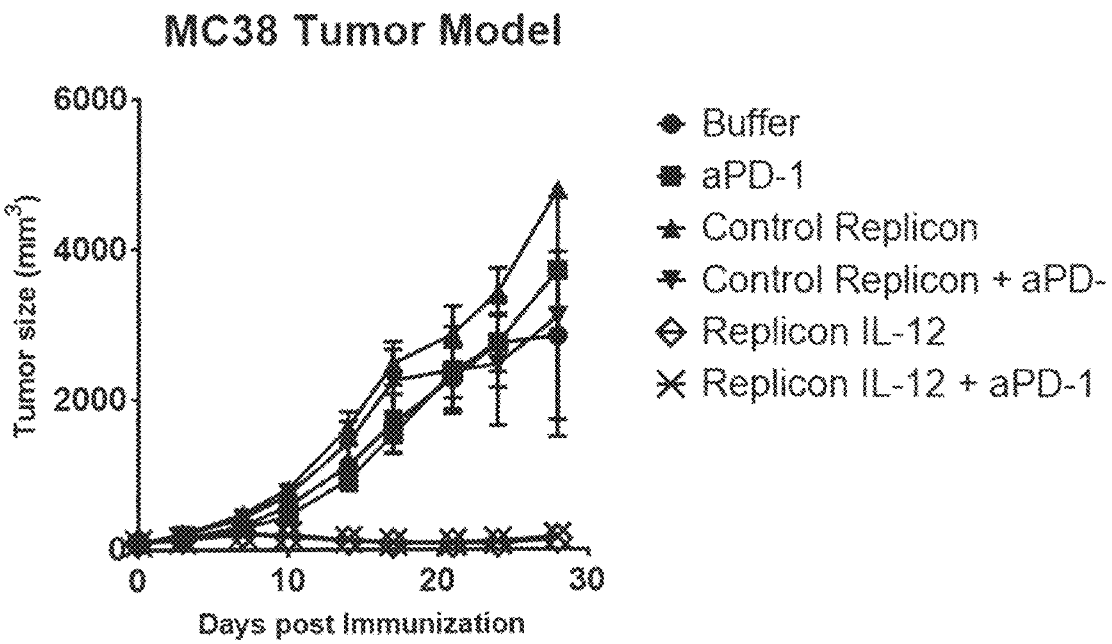
FIG. 4 Effect of IL-12 alphavirus replicon constructed to express construct 1 on MC-38 tumor model mice.

Results are shown in FIG. 4.

The data indicated that the IL-12 alphavirus replicon and the combination of IL-12 alphavirus replicon and anti-PD-1 antibody demonstrated superior anti-tumor effect over control and anti-PD-1 single immunotherapy.

Example 6

Effects of the Alphavirus Replicon Constructed to Express Construct 1

Figure 5:
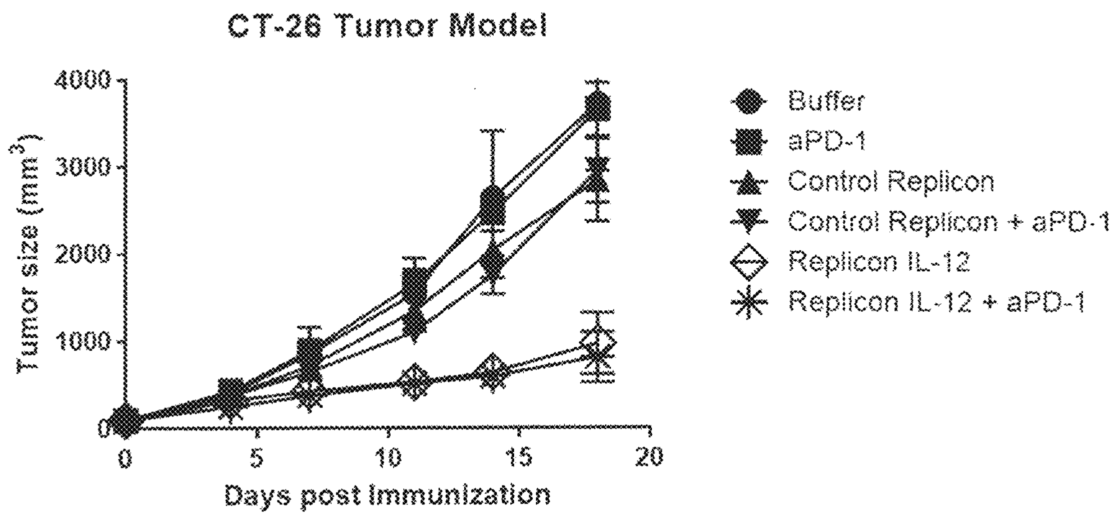
FIG. 5 Effect of IL-12 alphavirus replicon constructed to express construct 1 on CT-26 tumor model mice.

IL-12 alphavirus replicon particles (ARP) prepared in Example 4 constructed to express construct 1 were evaluated by using another cancer cell line. In this example, mouse CT-26 subcutaneous syngeneic mouse model was used. CT-26 is an N-nitroso-N-methylurethane-(NNMU) induced, undifferentiated colon carcinoma cell line. Balb/c female mice (48 mice) were injected with $5\times10^5$ cells subcutaneously into the rear flank. All mice were randomized into 6 groups (n=8 per group) when the average tumor volume reached 75-125 $mm^3$. Dosing was initiated within 24 hours of randomization (Day 0). Animals were dosed according to Table 2. The alphavirus replicon particles Group 3 and 4 were constructed to express GFP as a control vector and Groups 5 and 6 were constructed to express mouse IL-12 (Construct 1). The mice were injected with $4\times10^8$ infectious units (IU) of the indicated replicon intratumorally (i.t.) at one day intervals (total 8 injections) or with 10 mg/kg of an anti-mouse PD-1 monoclonal antibody (clone RMP1-14, aPD-1 mAb) given by intraperitoneal injection (IP), biweekly, for a total of 6 times. Animals were monitored and tumors were measured twice weekly for the duration of the study. The results are shown in FIG. 5. FIG. 5 shows mean and standard error of the mean (s.e.m.) of tumor size in each group.

TABLE 2

| Group | Treatment | N | Dose Route | Dosing Frequency & Duration | Dose Level (mg/kg) | Dose Volume (mL/kg) |
|---|---|---|---|---|---|---|
| 1 | Vehicle (TNE buffer) | 8 | i.t. | 0, 2, 4, 6, 8, 10, 12, 14 | NA | 50 ul for each dose (Fixed volume) |
| 2 | aPD-1 mAb | 8 | IP | BIWX3 weeks (Total 6 dose) | 10 | 5 |
| 3 | Control ARP (GFP) | 8 | i.t. | 0, 2, 4, 6, 8, 10, 12, 14 | $4 \times 10^8$ IU/dose | 50 ul for each dose (Fixed volume) |
| 4 | Control ARP (GFP) | 8 | i.t. | 0, 2, 4, 6, 8, 10, 12, 14 | $4 \times 10^8$ IU/dose | 50 ul for each dose (Fixed volume) |
| | aPD-1 mAb | 8 | IP | BIWX3 weeks (Total 6 dose) | 10 | 5 |
| 5 | ARP IL-12 | 8 | i.t. | 0, 2, 4, 6, 8, 10, 12, 14 | $4 \times 10^8$ IU/dose | 50 ul for each dose (Fixed volume) |
| 6 | ARP IL-12 | 8 | i.t. | 0, 2, 4, 6, 8, 10, 12, 14 | $4 \times 10^8$ IU/dose | 50 ul for each dose (Fixed volume) |
| | aPD-1 mAb | 8 | IP | BIWX3 weeks (Total 6 dose) | 10 | 5 |

The data indicated that IL-12 alphavirus replicon and the combination of IL-12 alphavirus replicon and anti-PD-1 antibody demonstrated superior anti-tumor effect over control and anti-PD-1 single immunotherapy.

Example 7

Effects of the Alphavirus Replicon Constructed to Express Construct 6

Figure 6A:
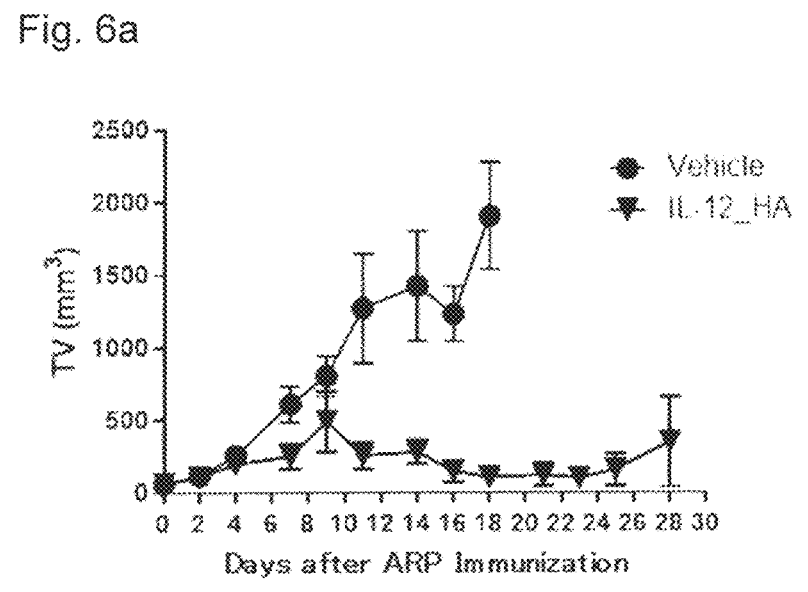
Figure 6B:
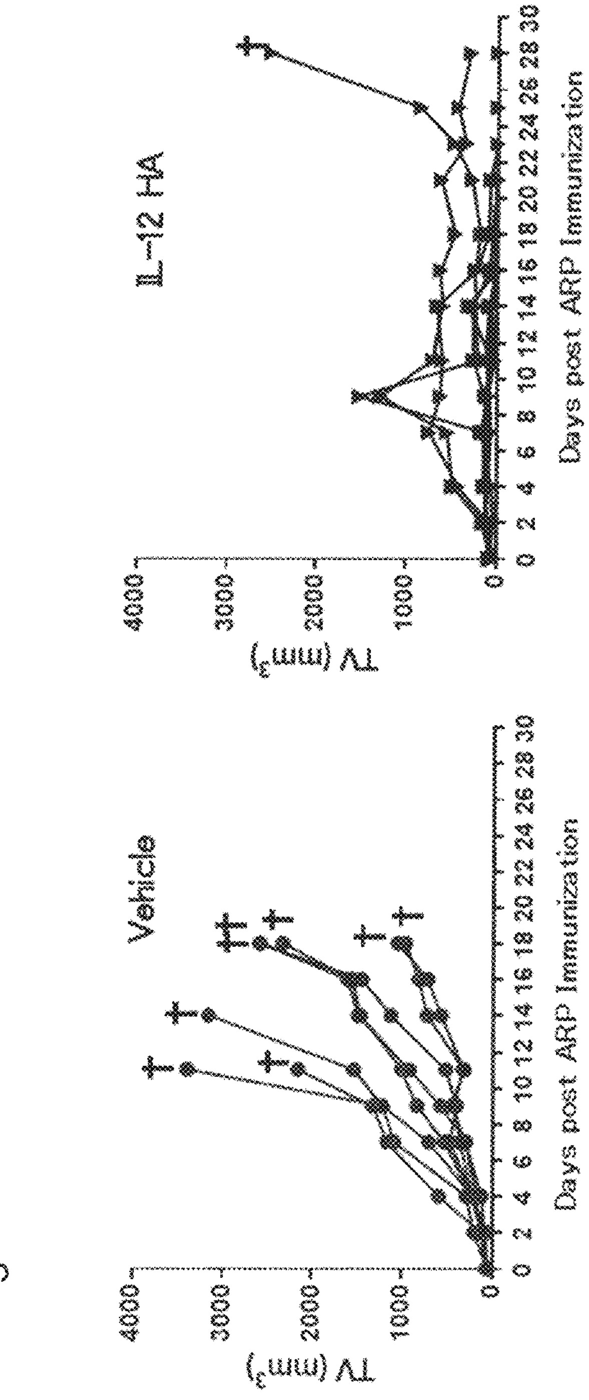
FIG. 6*b* Effect of IL-12 alphavirus replicon constructed to express construct 6 on CT-26 tumor model mice.

IL-12 alphavirus replicon particles prepared in Example 4 constructed to express construct 6 were evaluated. Balb/c female mice were injected with $1.75\times10^8$ CT-26 cells subcutaneously into the rear flank. All mice were randomized into 2 groups (n=8 per group) when the average tumor volume reached 50-100 mm$^3$. Dosing was initiated within 24 hours of randomization (Day 0). Animals were immunized with alphavirus replicon particles prepared in Example 4 expressing construct 6. The mice were injected with $4\times10^8$ infectious units (IU) of the indicated replicon intratumorally (i.t.) at one day intervals (total 8 injections). Animals were monitored and tumors were measured twice weekly for the duration of the study. The results are shown in FIG. 6*a*. FIG. 6*a* shows mean and standard error of the mean (s.e.m.) of tumor size in each group. FIG. 6*b* show tumor size of individual mouse (Left, vehicle, right, IL-12 HA). The cross symbols represent when each individual mouse was sacrificed due to large size of tumor.

The data indicates that IL-12 alphavirus replicon demonstrated potent anti-tumor effect.

Example 8

Effects of the Alphavirus Replicon Constructed to Express Construct 1

Figure 7A:
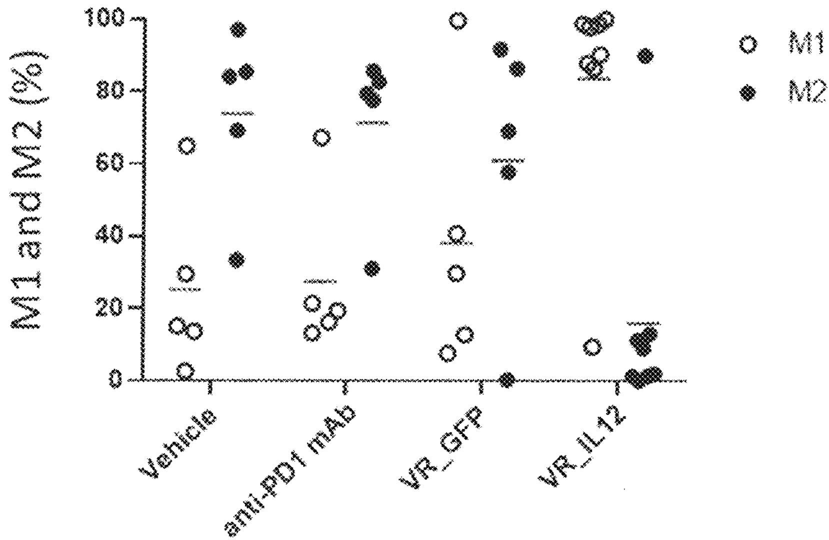
FIG. 7*a* Effect of IL-12 alphavirus replicon constructed to express construct 1 on macrophage M1 and M2 populations in TIL of MC-38 tumor model mice.
Figure 7B:
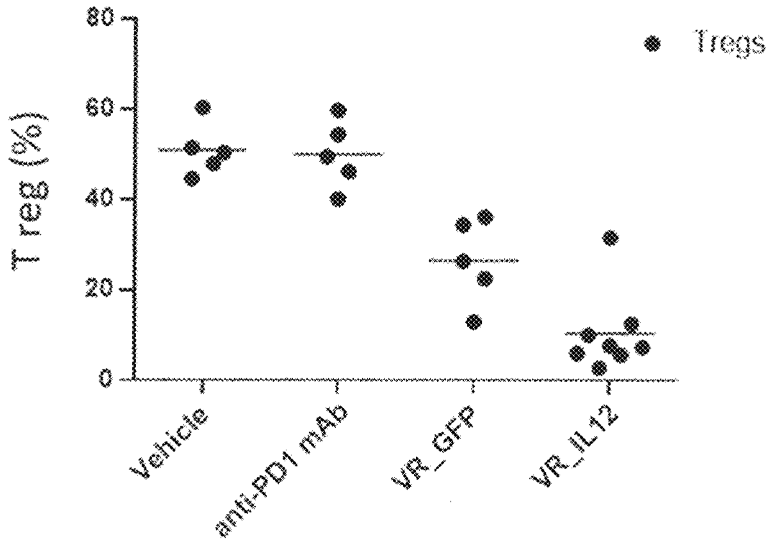
FIG. 7*b* Effect of IL-12 alphavirus replicon constructed to express construct 1 on Treg population in TIL of MC-38 tumor model mice.

IL-12 alphavirus replicon particles prepared in Example 4 constructed to express construct 1 were evaluated. C57BL6 female mice were injected with MC-38 cells subcutaneously into the rear flank. All mice were randomized into 4 groups (n=8 per group) when the average tumor volume reached 50-100 mm$^3$. Dosing was initiated within 24 hours of randomization (Day 0). The alphavirus replicon particles were constructed to express GFP as a control vector or to express mouse IL-12 (Construct 1). The mice were injected with $2.1\times10^8$ infectious units (IU) of the indicated replicon intratumorally (i.t.) at one day intervals (total 4 injections) on Day 0, 2, 4 and 6 or with 10 mg/kg of an anti-mouse PD-1 monoclonal antibody (clone RMP1-14, aPD-1 mAb) given by intraperitoneal injection (IP) on day 0 and 6. Animals were scarified on Day 9 and tumors collected and analyzed tumor-infiltrating lymphocytes (TIL) by FACS. The results are shown in FIG. 7. FIG. 7*a* shows M1 and M2 macrophage populations in macrophages contained in the TIL. Among the CD45$^+$CD11b$^+$F4/80$^+$ cells in the viable cells in TIL, M1 and M2 populations were identified by the markers of CD206 and IA/EA. FIG. 7*b* shows percentage of T regulatory cell (Treg) population in CD4$^+$ T cells contained in the TIL. Among the CD45$^+$CD3$^+$CD4$^+$ cells in the TIL, the percentage of FoxP3$^+$ cells was determined as Treg population. The mice immunized with replicon expressing mouse IL-12 shows that 1) population of M1 macrophage was much higher compared to population of M2 macrophage and 2) the population of Treg cells in TIL was reduced.

Although not intended to be constrained by theory, the present inventor considers that the alphavirus replicon constructed to express IL-12 can provide potent anti-tumor effect by increasing the M1 macrophage population over the M2 macrophage and also by reducing the Treg population in the TIL, in addition to the other known effects exerted by IL-12.

Example 9

Effects of the Alphavirus Replicon Constructed to Express Construct 1

C57BL6 female mice were injected with B16F10 cells subcutaneously into the rear flank. All mice were randomized into 6 groups (n=8 per group) when the average tumor volume reached 50-100 mm$^3$. B16F10 is a mouse cell line derived from melanoma. Dosing was initiated within 24 hours of randomization (Day 0). The alphavirus replicon particles were constructed to express GFP as a control vector or express mouse IL-12 (construct 1). The mice were injected with $1\times10^9$ infectious units (IU) of the indicated replicon intratumorally (i.t.) at one day intervals (total 8 injections) or with 10 mg/kg of an anti-mouse PD-1 monoclonal antibody (clone RMP1-14, aPD-1 mAb) given by intraperitoneal injection (IP) (total 6 injections). Animals were monitored and tumors were measured twice weekly for the duration of the study. The results are shown in FIG. 8. FIG. 8 shows mean and standard error of the mean (s.e.m.) of tumor size in each group.

The data indicated that IL-12 alphavirus replicon and the combination of IL-12 alphavirus replicon and anti-PD-1 antibody demonstrated superior anti-tumor effect over control and anti-PD-1 single immunotherapy.

What is claimed is:

1. An alphavirus replicon vector comprising, a polynucleotide which encodes (i) VEEV non-structural proteins nsp1, nsp2, nsp3 and nsp4, and (ii) a polypeptide comprising a cytokine which has the amino acid sequence of SEQ ID NO: 14.

2. The alphavirus replicon vector according to claim 1, wherein the VEEV non-structural proteins nsp1, nsp2, nsp3 and nsp4 have the amino acid sequence of SEQ ID NO: 23.

3. The alphavirus replicon vector according to claim 1, wherein the cytokine is fused to a transmembrane domain.

4. The alphavirus replicon vector according to claim 3, wherein the transmembrane domain is derived from Influenza Hemagglutinin (HA) or TLR4.

5. The alphavirus replicon vector according to claim 3, wherein the transmembrane domain is fused to the cytokine by a linker.

6. The alphavirus replicon vector according to claim 5, wherein the linker is IgG4CH3.

7. The alphavirus replicon vector according to claim 1, which comprises a promoter, 5' UTR, polynucleotide encoding VEEV non-structural proteins comprising the amino acid sequence of SEQ ID NO: 23, SG promoter, a gene of interest encoding a polypeptide comprising the amino acid sequence of SEQ ID NO: 14, 3'UTR and poly A tail.

8. A composition comprising (i) a pharmaceutically acceptable carrier, and (ii) the alphavirus replicon vector according to claim 1.

9. The composition according to claim 8, wherein the pharmaceutically acceptable carrier is a delivery vehicle and the alphavirus replicon vector is encapsulated in the delivery vehicle.

10. The composition according to claim 9, wherein the delivery vehicle is a particle consisting of alphavirus structural proteins or a lipid delivery system.

11. The composition according to claim 10, wherein the alphavirus structural proteins comprise a capsid and at least one envelope proteins and the capsid have one or more alterations in the Nuclear Localization Signal (NLS).

12. The particle according to claim 10, wherein the alphavirus structural proteins comprise at least one envelope protein E3 which comprises one or more alterations at the furin site in the E3 protein.

13. The composition comprising a lipid nanoparticle and the alphavirus replicon vector according to claim 1, wherein the alphavirus replicon vector is encapsulated in the lipid nanoparticle.

14. A vaccine comprising the alphavirus replicon vector according to claim 1.

15. A combination of the alphavirus replicon vector according to claim 1 and a checkpoint inhibitor polypeptide.

16. The combination according to claim 15, wherein the checkpoint inhibitor is an anti-PD-1 antibody.

17. A method of treating and/or immunizing against cancer or inflammatory disease in a subject, which comprises administering an effective amount of the alphavirus replicon vector according to claim 1 to the subject in need thereof.

18. A method of treating and/or immunizing against cancer or inflammatory disease in a subject, which comprises administering an effective amount of the combination according to claim 15 to the subject in need thereof.

* * * * *

SEQUENCE LISTING

```
Sequence total quantity: 24
SEQ ID NO: 1            moltype = AA  length = 539
FEATURE                 Location/Qualifiers
REGION                  1..539
                        note = Synthetic sequence, fused polypeptide comprising
                         mouse IL-12B p40, linker and mouse IL-12A p35 without
                         singal sequence (Mouse IL-12 (p40-p35))
source                  1..539
                        mol_type = protein
                        organism = synthetic construct
SEQUENCE: 1
MACPQKLTIS WFAIVLLVSP LMAMWELEKD VYVVEVDWTP DAPGETVNLT CDTPEEDDIT  60
WTSDQRHGVI GSGKTLTITV KEFLDAGQYT CHKGGETLSH SHLLLHKKEN GIWSTEILKN  120
FKNKTFLKCE APNYSGRFTC SWLVQRNMDL KFNIKSSSSP PDSRAVTCGM ASLSAEKVTL  180
DQRDYEKYSV SCQEDVTCPT AEETLPIELA LEARQQNKYE NYSTSFFIRD IIKPDPPKNL  240
QMKPLKNSQV EVSWEYPDSW STPHSYFSLK FFVRIQRKKE KMKETEEGCN QKGAFLVEKT  300
```

-continued

```
STEVQCKGGN VCVQAQDRYY NSSCSKWACV PCRVRSVPGV GVPGVGRVIP VSGPARCLSQ  360
SRNLLKTTDD MVKTAREKLK HYSCTAEDID HEDITRDQTS TLKTCLPLEL HKNESCLATR  420
ETSSTTRGSC LPPQKTSLMM TLCLGSIYED LKMYQTEFQA INAALQNHNH QQIILDKGML  480
VAIDELMQSL NHNGETLRQK PPVGEADPYR VKMKLCILLH AFSTRVVTIN RVMGYLSSA   539

SEQ ID NO: 2            moltype = AA  length = 336
FEATURE                 Location/Qualifiers
REGION                  1..336
                        note = Synthetic sequence, mouse IL-12B (p40)
source                  1..336
                        mol_type = protein
                        organism = synthetic construct
SEQUENCE: 2
MACPQKLTIS WFAIVLLVSP LMAMWELEKD VYVVEVDWTP DAPGETVNLT CDTPEEDDIT  60
WTSDQRHGVI GSGKTLTITV KEFLDAGQYT CHKGGETLSH SHLLLHKKEN GIWSTEILKN  120
FKNKTFLKCE APNYSGRFTC SWLVQRNMDL KFNIKSSSSP PDSRAVTCGM ASLSAEKVTL  180
DQRDYEKYSV SCQEDVTCPT AEETLPIELA LEARQQNKYE NYSTSFFIRD IIKPDPPKNL  240
QMKPLKNSQV EVSWEYPDSW STPHSYFSLK FFVRIQRKKE KMKETEEGCN QKGAFLVEKT  300
STEVQCKGGN VCVQAQDRYY NSSCSKWACV PCRVRS                            336

SEQ ID NO: 3            moltype = AA  length = 193
FEATURE                 Location/Qualifiers
REGION                  1..193
                        note = Synthetic sequence, mouse IL-12A (35p) without
                         signal sequence
source                  1..193
                        mol_type = protein
                        organism = synthetic construct
SEQUENCE: 3
RVIPVSGPAR CLSQSRNLLK TTDDMVKTAR EKLKHYSCTA EDIDHEDITR DQTSTLKTCL  60
PLELHKNESC LATRETSSTT RGSCLPPQKT SLMMTLCLGS IYEDLKMYQT EFQAINAALQ  120
NHNHQQIILD KGMLVAIDEL MQSLNHNGET LRQKPPVGEA DPYRVKMKLC ILLHAFSTRV  180
VTINRVMGYL SSA                                                     193

SEQ ID NO: 4            moltype = AA  length = 10
FEATURE                 Location/Qualifiers
REGION                  1..10
                        note = Synthetic sequence, linker
source                  1..10
                        mol_type = protein
                        organism = synthetic construct
SEQUENCE: 4
VPGVGVPGVG                                                         10

SEQ ID NO: 5            moltype = AA  length = 698
FEATURE                 Location/Qualifiers
REGION                  1..698
                        note = Synthetic sequence, fused plypeptide comprising
                         mouse IL-12(p40-p35), Human IgG4CH3 and Influenza
                         HA(flex-TM-Cyt)
source                  1..698
                        mol_type = protein
                        organism = synthetic construct
SEQUENCE: 5
MACPQKLTIS WFAIVLLVSP LMAMWELEKD VYVVEVDWTP DAPGETVNLT CDTPEEDDIT  60
WTSDQRHGVI GSGKTLTITV KEFLDAGQYT CHKGGETLSH SHLLLHKKEN GIWSTEILKN  120
FKNKTFLKCE APNYSGRFTC SWLVQRNMDL KFNIKSSSSP PDSRAVTCGM ASLSAEKVTL  180
DQRDYEKYSV SCQEDVTCPT AEETLPIELA LEARQQNKYE NYSTSFFIRD IIKPDPPKNL  240
QMKPLKNSQV EVSWEYPDSW STPHSYFSLK FFVRIQRKKE KMKETEEGCN QKGAFLVEKT  300
STEVQCKGGN VCVQAQDRYY NSSCSKWACV PCRVRSVPGV GVPGVGRVIP VSGPARCLSQ  360
SRNLLKTTDD MVKTAREKLK HYSCTAEDID HEDITRDQTS TLKTCLPLEL HKNESCLATR  420
ETSSTTRGSC LPPQKTSLMM TLCLGSIYED LKMYQTEFQA INAALQNHNH QQIILDKGML  480
VAIDELMQSL NHNGETLRQK PPVGEADPYR VKMKLCILLH AFSTRVVTIN RVMGYLSSAG  540
SGQPREPQVY TLPPSQEEMT KNQVSLTCLV KGFYPSDIAV EWESNGQPEN NYKTTPPVLD  600
SDGSFFLYSR LTVDKSRWQE GNVFSCSVMH EALHNHYTQK SLSLSLGKGS GVKLESMGIY  660
QILAIYSTVA SSLVLLVSLG AISFWMCSNG SLQCRICI                          698

SEQ ID NO: 6            moltype = AA  length = 107
FEATURE                 Location/Qualifiers
REGION                  1..107
                        note = Synthetic sequence, human IgG4CH3
source                  1..107
                        mol_type = protein
                        organism = synthetic construct
SEQUENCE: 6
GQPREPQVYT LPPSQEEMTK NQVSLTCLVK GFYPSDIAVE WESNGQPENN YKTTPPVLDS  60
DGSFFLYSRL TVDKSRWQEG NVFSCSVMHE ALHNHYTQKS LSLSLGK                107

SEQ ID NO: 7            moltype = AA  length = 48
```

-continued

```
FEATURE                Location/Qualifiers
REGION                 1..48
                       note = Synthetic sequence, influenza HA(flexible-TM-Cyt)
source                 1..48
                       mol_type = protein
                       organism = synthetic construct
SEQUENCE: 7
GVKLESMGIY QILAIYSTVA SSLVLLVSLG AISFWMCSNG SLQCRICI              48

SEQ ID NO: 8           moltype = AA  length = 589
FEATURE                Location/Qualifiers
REGION                 1..589
                       note = Synthetic sequence, fused polypeptide comprising
                        mouse IL-12(p40-p35) and influenza HA(Flex-TM-Cyt)
source                 1..589
                       mol_type = protein
                       organism = synthetic construct
SEQUENCE: 8
MACPQKLTIS WFAIVLLVSP LMAMWELEKD VYVVEVDWTP DAPGETVNLT CDTPEEDDIT  60
WTSDQRHGVI GSGKTLTITV KEFLDAGQYT CHKGGETLSH SHLLLHKKEN GIWSTEILKN  120
FKNKTFLKCE APNYSGRFTC SWLVQRNMDL KFNIKSSSSP PDSRAVTCGM ASLSAEKVTL  180
DQRDYEKYSV SCQEDVTCPT AEETLPIELA LEARQQNKYE NYSTSFFIRD IIKPDPPKNL  240
QMKPLKNSQV EVSWEYPDSW STPHSYFSLK FFVRIQRKKE KMKETEEGCN QKGAFLVEKT  300
STEVQCKGGN VCVQAQDRYY NSSCSKWACV PCRVRSVPGV GVPGVGRVIP VSGPARCLSQ  360
SRNLLKTTDD MVKTAREKLK HYSCTAEDID HEDITRDQTS TLKTCLPLEL HKNESCLATR  420
ETSSTTRGSC LPPQKTSLMM TLCLGSIYED LKMYQTEFQA INAALQNHNH QQIILDKGML  480
VAIDELMQSL NHNGETLRQK PPVGEADPYR VKMKLCILLH AFSTRVVTIN RVMGYLSSAG  540
SGVKLESMGI YQILAIYSTV ASSLVLLVSL GAISFWMCSN GSLQCRICI              589

SEQ ID NO: 9           moltype = AA  length = 859
FEATURE                Location/Qualifiers
REGION                 1..859
                       note = Synthetic sequence, fused polypeptide comprising
                        mouse IL-12 (p40-p35), human IgG4CH3 and human TLR4(TM-TIR)
source                 1..859
                       mol_type = protein
                       organism = synthetic construct
SEQUENCE: 9
MACPQKLTIS WFAIVLLVSP LMAMWELEKD VYVVEVDWTP DAPGETVNLT CDTPEEDDIT  60
WTSDQRHGVI GSGKTLTITV KEFLDAGQYT CHKGGETLSH SHLLLHKKEN GIWSTEILKN  120
FKNKTFLKCE APNYSGRFTC SWLVQRNMDL KFNIKSSSSP PDSRAVTCGM ASLSAEKVTL  180
DQRDYEKYSV SCQEDVTCPT AEETLPIELA LEARQQNKYE NYSTSFFIRD IIKPDPPKNL  240
QMKPLKNSQV EVSWEYPDSW STPHSYFSLK FFVRIQRKKE KMKETEEGCN QKGAFLVEKT  300
STEVQCKGGN VCVQAQDRYY NSSCSKWACV PCRVRSVPGV GVPGVGRVIP VSGPARCLSQ  360
SRNLLKTTDD MVKTAREKLK HYSCTAEDID HEDITRDQTS TLKTCLPLEL HKNESCLATR  420
ETSSTTRGSC LPPQKTSLMM TLCLGSIYED LKMYQTEFQA INAALQNHNH QQIILDKGML  480
VAIDELMQSL NHNGETLRQK PPVGEADPYR VKMKLCILLH AFSTRVVTIN RVMGYLSSAG  540
SGQPREPQVY TLPPSQEEMT KNQVSLTCLV KGFYPSDIAV EWESNGQPEN NYKTTPPVLD  600
SDGSFFLYSR LTVDKSRWQE GNVFSCSVMH EALHNHYTQK SLSLSLGKGS KTIIGVSVLS  660
VLVVSVVAVL VYKFYFHLML LAGCIKYGRG ENIYDAFVIY SSQDEDWVRN ELVKNLEEGV  720
PPFQLCLHYR DFIPGVAIAA NIIHEGFHKS RKVIVVVSQH FIQSRWCIFE YEIAQTWQFL  780
SSRAGIIFIV LQKVEKTLLR QQVELYRLLS RNTYLEWEDS VLGRHIFWRR LRKALLDGKS  840
WNPEGTVGTG CNWQEATSI                                               859

SEQ ID NO: 10          moltype = AA  length = 209
FEATURE                Location/Qualifiers
REGION                 1..209
                       note = Synthetic sequence, human TLR4(TM-TIR)
source                 1..209
                       mol_type = protein
                       organism = synthetic construct
SEQUENCE: 10
KTIIGVSVLS VLVVSVVAVL VYKFYFHLML LAGCIKYGRG ENIYDAFVIY SSQDEDWVRN  60
ELVKNLEEGV PPFQLCLHYR DFIPGVAIAA NIIHEGFHKS RKVIVVVSQH FIQSRWCIFE  120
YEIAQTWQFL SSRAGIIFIV LQKVEKTLLR QQVELYRLLS RNTYLEWEDS VLGRHIFWRR  180
LRKALLDGKS WNPEGTVGTG CNWQEATSI                                   209

SEQ ID NO: 11          moltype = AA  length = 750
FEATURE                Location/Qualifiers
REGION                 1..750
                       note = Synthetic sequence, fused polypeptide comprising
                        mouse IL-12(p40-p35) and human TLR4(TM-TIR)
source                 1..750
                       mol_type = protein
                       organism = synthetic construct
SEQUENCE: 11
MACPQKLTIS WFAIVLLVSP LMAMWELEKD VYVVEVDWTP DAPGETVNLT CDTPEEDDIT  60
WTSDQRHGVI GSGKTLTITV KEFLDAGQYT CHKGGETLSH SHLLLHKKEN GIWSTEILKN  120
FKNKTFLKCE APNYSGRFTC SWLVQRNMDL KFNIKSSSSP PDSRAVTCGM ASLSAEKVTL  180
```

```
DQRDYEKYSV SCQEDVTCPT AEETLPIELA LEARQQNKYE NYSTSFFIRD IIKPDPPKNL  240
QMKPLKNSQV EVSWEYPDSW STPHSYFSLK FFVRIQRKKE KMKETEEGCN QKGAFLVEKT  300
STEVQCKGGN VCVQAQDRYY NSSCSKWACV PCRVRSVPGV GVPGVGRVIP VSGPARCLSQ  360
SRNLLKTTDD MVKTAREKLK HYSCTAEDID HEDITRDQTS TLKTCLPLEL HKNESCLATR  420
ETSSTTRGSC LPPQKTSLMM TLCLGSIYED LKMYQTEFQA INAALQNHNH QQIILDKGML  480
VAIDELMQSL NHNGETLRQK PPVGEADPYR VKMKLCILLH AFSTRVVTIN RVMGYLSSAG  540
SKTIIGVSVL SVLVVSVVAV LVYKFYFHLM LLAGCIKYGR GENIYDAFVI YSSQDEDWVR  600
NELVKNLEEG VPPFQLCLHY RDFIPGVAIA ANIIHEGFHK SRKVIVVVSQ HFIQSRWCIF  660
EYEIAQTWQF LSSRAGIIFI VLQKVEKTLL RQQVELYRLL SRNTYLEWED SVLGRHIFWR  720
RLRKALLDGK SWNPEGTVGT GCNWQEATSI                                  750

SEQ ID NO: 12           moltype = AA  length = 698
FEATURE                 Location/Qualifiers
REGION                  1..698
                        note = Synthetic sequence, fused polypeptide comprising
                         mouse IL-12(p40-p35), mouse IgG4CH3 and influenza
                         HA(Flex-TM-Cyt)
source                  1..698
                        mol_type = protein
                        organism = synthetic construct
SEQUENCE: 12
MACPQKLTIS WFAIVLLVSP LMAMWELEKD VYVVEVDWTP DAPGETVNLT CDTPEEDDIT  60
WTSDQRHGVI GSGKTLTITV KEFLDAGQYT CHKGGETLSH SHLLLHKKEN GIWSTEILKN  120
FKNKTFLKCE APNYSGRFTC SWLVQRNMDL KFNIKSSSSP PDSRAVTCGM ASLSAEKVTL  180
DQRDYEKYSV SCQEDVTCPT AEETLPIELA LEARQQNKYE NYSTSFFIRD IIKPDPPKNL  240
QMKPLKNSQV EVSWEYPDSW STPHSYFSLK FFVRIQRKKE KMKETEEGCN QKGAFLVEKT  300
STEVQCKGGN VCVQAQDRYY NSSCSKWACV PCRVRSVPGV GVPGVGRVIP VSGPARCLSQ  360
SRNLLKTTDD MVKTAREKLK HYSCTAEDID HEDITRDQTS TLKTCLPLEL HKNESCLATR  420
ETSSTTRGSC LPPQKTSLMM TLCLGSIYED LKMYQTEFQA INAALQNHNH QQIILDKGML  480
VAIDELMQSL NHNGETLRQK PPVGEADPYR VKMKLCILLH AFSTRVVTIN RVMGYLSSAG  540
SGRPKAPQVY TIPPPKEQMA KDKVSLTCMI TNFFPEDITV EWQWNGQPAE NYKNTQPIMD  600
TDGSYFVYSK LNVQKSNWEA GNTFTCSVLH EGLHNHHTEK SLSHSPGKGS GVKLESMGIY  660
QILAIYSTVA SSLVLLVSLG AISFWMCSNG SLQCRICI                         698

SEQ ID NO: 13           moltype = AA  length = 106
FEATURE                 Location/Qualifiers
REGION                  1..106
                        note = Synthetic sequence, mouse IgG4CH3
source                  1..106
                        mol_type = protein
                        organism = synthetic construct
SEQUENCE: 13
GRPKAPQVYT IPPPKEQMAK DKVSLTCMIT NFFPEDITVE WQWNGQPAEN YKNTQPIMDT  60
DGSYFVYSKL NVQKSNWEAG NTFTCSVLHE GLHNHHTEKS LSHSPG                106

SEQ ID NO: 14           moltype = AA  length = 535
FEATURE                 Location/Qualifiers
REGION                  1..535
                        note = Synthetic sequence, fused polypeptide comprising
                         human IL-12B p40, linker and human IL-12A p35 without
                         singal sequence (Human IL-12(p40-p35))
source                  1..535
                        mol_type = protein
                        organism = synthetic construct
SEQUENCE: 14
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSVP GVGVPGVGRN LPVATPDPGM FPCLHHSQNL  360
LRAVSNMLQK ARQTLEFYPC TSEEIDHEDI TKDKTSTVEA CLPLELTKNE SCLNSRETSF  420
ITNGSCLASR KTSFMMALCL SSIYEDLKMY QVEFKTMNAK LLMDPKRQIF LDQNMLAVID  480
ELMQALNFNS ETVPQKSSLE EPDFYKTKIK LCILLHAFRI RAVTIDRVMS YLNAS       535

SEQ ID NO: 15           moltype = AA  length = 328
FEATURE                 Location/Qualifiers
REGION                  1..328
                        note = Synthetic sequence, human IL-12B(p40)
source                  1..328
                        mol_type = protein
                        organism = synthetic construct
SEQUENCE: 15
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                                    328
```

```
SEQ ID NO: 16           moltype = AA  length = 22
FEATURE                 Location/Qualifiers
REGION                  1..22
                        note = Synthetic sequence, signal sequence of human IL-12A
                         (p35)
source                  1..22
                        mol_type = protein
                        organism = synthetic construct
SEQUENCE: 16
MCPARSLLLV ATLVLLDHLS LA                                              22

SEQ ID NO: 17           moltype = AA  length = 197
FEATURE                 Location/Qualifiers
REGION                  1..197
                        note = Synthetic sequence, human IL-12A (p35) without
                         signal sequence
source                  1..197
                        mol_type = protein
                        organism = synthetic construct
SEQUENCE: 17
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                197

SEQ ID NO: 18           moltype = AA  length = 694
FEATURE                 Location/Qualifiers
REGION                  1..694
                        note = Synthetic sequence, fused polypeptide comprising
                         human IL-12(p40-p35) , human IgG4CH3 and Influenza HA
                         (Flex-TM-Cyt)
source                  1..694
                        mol_type = protein
                        organism = synthetic construct
SEQUENCE: 18
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSVP GVGVPGVGRN LPVATPDPGM FPCLHHSQNL  360
LRAVSNMLQK ARQTLEFYPC TSEEIDHEDI TKDKTSTVEA CLPLELTKNE SCLNSRETSF  420
ITNGSCLASR KTSFMMALCL SSIYEDLKMY QVEFKTMNAK LLMDPKRQIF LDQNMLAVID  480
ELMQALNFNS ETVPQKSSLE EPDFYKTKIK LCILLHAFRI RAVTIDRVMS YLNASGSGQP  540
REPQVYTLPP SQEEMTKNQV SLTCLVKGFY PSDIAVEWES NGQPENNYKT TPPVLDSDGS  600
FFLYSRLTVD KSRWQEGNVF SCSVMHEALH NHYTQKSLSL SLGKGSGVKL ESMGIYQILA  660
IYSTVASSLV LLVSLGAISF WMCSNGSLQC RICI                              694

SEQ ID NO: 19           moltype = DNA  length = 35
FEATURE                 Location/Qualifiers
misc_feature            1..35
                        note = Synthetic sequence, SG promoter
source                  1..35
                        mol_type = other DNA
                        organism = synthetic construct
SEQUENCE: 19
cctgaatgga ctacgacata gtctagtccg ccaag                                35

SEQ ID NO: 20           moltype = DNA  length = 44
FEATURE                 Location/Qualifiers
misc_feature            1..44
                        note = Synthetic sequence, 5'UTR
source                  1..44
                        mol_type = other DNA
                        organism = synthetic construct
SEQUENCE: 20
ataggcggcg catgagagaa gcccagacca attacctacc caaa                      44

SEQ ID NO: 21           moltype = DNA  length = 125
FEATURE                 Location/Qualifiers
misc_feature            1..125
                        note = Synthetic sequence, 3'UTR
source                  1..125
                        mol_type = other DNA
                        organism = synthetic construct
SEQUENCE: 21
gcgatcgcat acagcagcaa ttggcaagct gcttacatag aactcgcggc gattggcatg  60
ccgccttaaa atttttattt tatttttctt ttcttttccg aatcggattt tgtttttaat  120
```

```
atttc                                                        125

SEQ ID NO: 22           moltype = DNA  length = 55
FEATURE                 Location/Qualifiers
misc_feature            1..55
                        note = Synthetic sequence, poly A tail
source                  1..55
                        mol_type = other DNA
                        organism = synthetic construct
SEQUENCE: 22
aaaaaaaaaa aaaaaaaaaa aaaaaaaaaa aaaaaaaaaa aaaaaaaaaa aaaaa      55

SEQ ID NO: 23           moltype = AA  length = 2493
FEATURE                 Location/Qualifiers
REGION                  1..2493
                        note = Synthetic sequence, VEEV TC-83 Replicon nsP1-4
SITE                    1880
                        note = misc_feature - Xaa can be any naturally occurring
                         amino acid
source                  1..2493
                        mol_type = protein
                        organism = synthetic construct
SEQUENCE: 23
MEKVHVDIEE DSPFLRALQR SFPQFEVEAK QVTDNDHANA RAFSHLASKL IETEVDPSDT  60
ILDIGSAPAR RMYSKHKYHC ICPMRCAEDP DRLYKYATKL KKNCKEITDK ELDKKMKELA  120
AVMSDPDLET ETMCLHDDES CRYEGQVAVY QDVYAVDGPT SLYHQANKGV RVAYWIGFDT  180
TPFMFKNLAG AYPSYSTNWA DETVLTARNI GLCSSDVMER SRRGMSILRK KYLKPSNNVL  240
FSVGSTIYHE KRDLLRSWHL PSVFHLRGKQ NYTCRCETIV SCDGYVVKRI AISPGLYGKP  300
SGYAATMHRE GFLCCKVTDT LNGERVSFPV CTYVPATLCD QMTGILATDV SADDAQKLLV  360
GLNQRIVVNG RTQRNTNTMK NYLLPVVAQA FARWAKEYKE DQEDERPLGL RDRQLVMGCC  420
WAFRRHKITS IYKRPDTQTI IKVNSDFHSF VLPRIGSNTL EIGLRTRIRK MLEEHKEPSP  480
LITAEDIQEA KCAADEAKEV REAEELRAAL PPLAADFEEP TLEADVDLML QEAGAGSVET  540
PRGLIKVTSY AGEDKIGSYA VLSPQAVLKS EKLSCIHPLA EQVIVITHSG RKGRYAVEPY  600
HGKVVVPEGH AIPVQDFQAL SESATIVYNE REFVNRYLHH IATHGGALNT DEEYYKTVKP  660
SEHDGEYLYD IDRKQCVKKE LVTGLGLTGE LVDPPFHEFA YESLRTRPAA PYQVPTIGVY  720
GVPGSGKSGI IKSAVTKKDL VVSAKKENCA EIIRDVKKMK GLDVNARTVD SVLLNGCKHP  780
VETLYIDEAF ACHAGTLRAL IAIIRPKKAV LCGDPKQCGF FNMMCLKVHF NHEICTQVFH  840
KSISRRCTKS VTSVVSTLFY DKRMRTTNPK ETKIVIDTTG STKPKQDDLI LTCFRGWVKQ  900
LQIDYKGNEI MTAAASQGLT RKGVYAVRYK VNENPLYAPT SEHVNVLLTR TEDRIVWKTL  960
AGDPWIKILT AKYPGNFTAT IEEWQAEHDA IMRHILERPD PTDVFQNKAN VCWAKALVPV  1020
LKTAGIDMTT EQWNTVDYFE TDKAHSAEIV LNQLCVRFFG LDLDSGLFSA PTVPLSIRNN  1080
HWDNSPSPNM YGLNKEVVRQ LSRRYPQLPR AVATGRVYDM NTGTLRNYDP RINLVPVNRR  1140
LPHALVLHHN EHPQSDFSSF VSKLKGRTVL VVGEKLSVPG KKVDWLSDQP EATFRARLDL  1200
GIPGDVPKYD IVFINVRTPY KYHHYQQCED HAIKLSMLTK KACLHLNPGG TCVSIGYGYA  1260
DRASESIIGA IARQFKFSRV CKPKSSHEET EVLFVFIGYD RKARTHNPYK LSSTLTNIYT  1320
GSRLHEAGCA PSYHVVRGDI ATATEGVIIN AANSKGQPGG GVCGALYKKF PESFDLQPIE  1380
VGKARLVKGA AKHIIHAVGP NFNKVSEVEG DKQLAEAYES IAKIVNDNNY KSVAIPLLST  1440
GIFSGNKDRL TQSLNHLLTA LDTTDADVAI YCRDKKWEMT LKEAVARREA VEEICISDDS  1500
SVTEPDAELV RVHPKSSLAG RKGYSTSDGK TFSYLEGTKF HQAAKDIAEI NAMWPVATEA  1560
NEQVCMYILG ESMSSIRSKC PVEESEASTP PSTLPCLCIH AMTPERVQRL KASRPEQITV  1620
CSSFPLPKYR ITGVQKIQCS QPILFSPKVP AYIHPRKYLV ETPPVEETPE SPAENQSTEG  1680
TPEQPALVNV DATRTRMPEP IIIEEEEDS ISLLSDGPTH QVLQVEADIH GSPSVSSSSW  1740
SIPHASDFDV DSLSILDTLD GASVTSGAVS AETNSYFARS MEFRARPVPA PRTVFRNPPH  1800
PAPRTRTPPL AHSRASSRTS LVSTPPGVNR VITREELEAL TPSRAPSRSA SRTSLVSNPP  1860
GVNRVITREE FEAFVAQQQX RFDAGAYIFS SDTGQGHLQQ KSVRQTVLSE VVLERTELEI  1920
SYAPRLDQEK EELLRKKLQL NPTPANRSRY QSRRVENMKA ITARRILQGL GHYLKAEGKV  1980
ECYRTLHPVP LYSSSVNRAF SSPKVAVEAC NAMLKENFPT VASYCIIPEY DAYLDMVDGA  2040
SCCLDTASFC PAKLRSFPKK HSYLEPTIRS AVPSAIQNTL QNVLAAATKR NCNVTQMREL  2100
PVLDSAAFNV ECFKKYACNN EYWETFKENP IRLTEENVVN YITKLKGPKA AALFAKTHNL  2160
NMLQDIPMDR FVMDLKRDVK VTPGTKHTEE RPKVQVIQAA DPLATADLCG IHRELVRRLN  2220
AVLLPNIHTL FDMSAEDFDA IIAEHFQPGD CVLETDIASF DKSEDDAMAL TALMILEDLG  2280
VDAELLTLIE AAFGEISSIH LPTKTKFKFG AMMKSGMFLT LFVNTVINIV IASRVLRERL  2340
TGSPCAAFIG DDNIVKGVKS DKLMADRCAT WLNMEVKIID AVVGEKAPYF CGGFILCDSV  2400
TGTACRVADP LKRLFKLGKP LAVDDEHDDD RRRALHEEST RWNRVGILPE LCKAVESRYE  2460
TVGTSIIVMA MTTLASSVKS FSYLRGAPIT LYG                             2493

SEQ ID NO: 24           moltype = AA  length = 557
FEATURE                 Location/Qualifiers
REGION                  1..557
                        note = Synthetic sequence, VEEV TC-83 nsp3 E242K
SITE                    551
                        note = misc_feature - Xaa can be any naturally occurring
                         amino acid
source                  1..557
                        mol_type = protein
                        organism = synthetic construct
SEQUENCE: 24
APSYHVVRGD IATATEGVII NAANSKGQPG GGVCGALYKK FPESFDLQPI EVGKARLVKG  60
AAKHIIHAVG PNFNKVSEVE GDKQLAEAYE SIAKIVNDNN YKSVAIPLLS TGIFSGNKDR  120
```

-continued

```
LTQSLNHLLT ALDTTDADVA IYCRDKKWEM TLKEAVARRE AVEEICISDD SSVTEPDAEL  180
VRVHPKSSLA GRKGYSTSDG KTFSYLEGTK FHQAAKDIAE INAMWPVATE ANEQVCMYIL  240
GKSMSSIRSK CPVEESEAST PPSTLPCLCI HAMTPERVQR LKASRPEQIT VCSSFPLPKY  300
RITGVQKIQC SQPILFSPKV PAYIHPRKYL VETPPVDETP EPSAENQSTE GTPEQPPLIT  360
EDETRTRTPE PIIIEEEEED SISLLSDGPT HQVLQVEADI HGPPSVSSSS WSIPHASDFD  420
VDSLSILDTL EGASVTSGAT SAETNSYFAK SMEFLARPVP APRTVFRNPP HPAPRTRTPS  480
LAPSRACSRT SLVSTPPGVN RVITREELEA LTPSRTPSRS VSRTSLVSNP PGVNRVITRE  540
EFEAFVAQQQ XRFDAGA                                                 557
```